(12) United States Patent
Draelos et al.

(10) Patent No.: US 10,888,389 B2
(45) Date of Patent: Jan. 12, 2021

(54) SYSTEMS AND METHODS FOR ARBITRARY VIEWPOINT ROBOTIC MANIPULATION AND ROBOTIC SURGICAL ASSISTANCE

(71) Applicant: Duke University, Durham, NC (US)

(72) Inventors: Mark Draelos, Durham, NC (US); Kris Hauser, Durham, NC (US); Anthony Kuo, Durham, NC (US); Brenton Keller, Durham, NC (US); Joseph Izatt, Durham, NC (US)

(73) Assignee: Duke University, Durham, NC (US)

( * ) Notice: Subject to any disclaimer, the term of this patent is extended or adjusted under 35 U.S.C. 154(b) by 364 days.

(21) Appl. No.: 15/755,125

(22) PCT Filed: Sep. 12, 2016

(86) PCT No.: PCT/US2016/051360
§ 371 (c)(1),
(2) Date: Feb. 26, 2018

(87) PCT Pub. No.: WO2017/044965
PCT Pub. Date: Mar. 16, 2017

(65) Prior Publication Data
US 2019/0015167 A1    Jan. 17, 2019

Related U.S. Application Data

(60) Provisional application No. 62/366,254, filed on Jul. 25, 2016, provisional application No. 62/216,652, filed on Sep. 10, 2015.

(51) Int. Cl.
*G05B 15/00*       (2006.01)
*A61B 34/00*       (2016.01)
(Continued)

(52) U.S. Cl.
CPC .............. *A61B 34/76* (2016.02); *A61B 34/10* (2016.02); *A61B 34/25* (2016.02); *A61B 34/30* (2016.02);
(Continued)

(58) Field of Classification Search
CPC ... A61B 2034/105; A61B 34/10; A61B 34/25; A61B 34/30; A61B 34/37; A61B 34/76; A61F 9/007
See application file for complete search history.

(56) References Cited

U.S. PATENT DOCUMENTS 7,907,166 B2    3/2011  Lamprecht et al.
2009/0192523 A1*  7/2009  Larkin .................... A61B 1/04
                                              606/130
(Continued)

OTHER PUBLICATIONS

International Preliminary Report on Patentability and Written Opinion issued in PCT Application No. PCT/US2016/051360 dated Mar. 13, 2018. (eight (8) pages).
(Continued)

*Primary Examiner* — Harry Y Oh
(74) *Attorney, Agent, or Firm* — Olive Law Group, PLLC

(57) ABSTRACT

Systems and methods for arbitrary viewpoint robotic manipulation and robotic surgical assistance are disclosed. According to an aspect, a system includes one or more controllers configured to receive an image dataset of an actual environment within which the robotic tool is positioned. The controller(s) are also configured to generate a virtual environment of the actual environment based on the image dataset. Further, the controller(s) can control display of the virtual environment including a virtual tool controllable by a user for use to control the robotic tool within the actual environment. The controller(s) can receive user input for altering a perspective view of display of the virtual environment from a first perspective view to a second
(Continued)

perspective view. Further, the controller(s) can maintain orientation of display of the virtual tool with respect to the user during display of the first perspective view and the second perspective view of the virtual environment.

27 Claims, 23 Drawing Sheets

(51) Int. Cl.
*A61B 34/37* (2016.01)
*A61B 34/10* (2016.01)
*A61B 34/30* (2016.01)
*A61F 9/007* (2006.01)

(52) U.S. Cl.
CPC .............. *A61B 34/37* (2016.02); *A61F 9/007* (2013.01); *A61B 2034/105* (2016.02)

(56) References Cited

U.S. PATENT DOCUMENTS

| | | | |
|---|---|---|---|
| 2010/0063508 A1* | 3/2010 | Borja | A61B 17/154 606/88 |
| 2010/0331858 A1* | 12/2010 | Simaan | A61B 34/37 606/130 |
| 2012/0226150 A1* | 9/2012 | Balicki | A61B 5/7475 600/424 |
| 2013/0245375 A1* | 9/2013 | DiMaio | A61B 34/37 600/111 |
| 2014/0275760 A1 | 9/2014 | Lee et al. | |

OTHER PUBLICATIONS

International Search Report and Written Opinion issued in PCT Application No. PCT/US2016/051360 dated Jan. 5, 2017 (ten (10) pages).

* cited by examiner

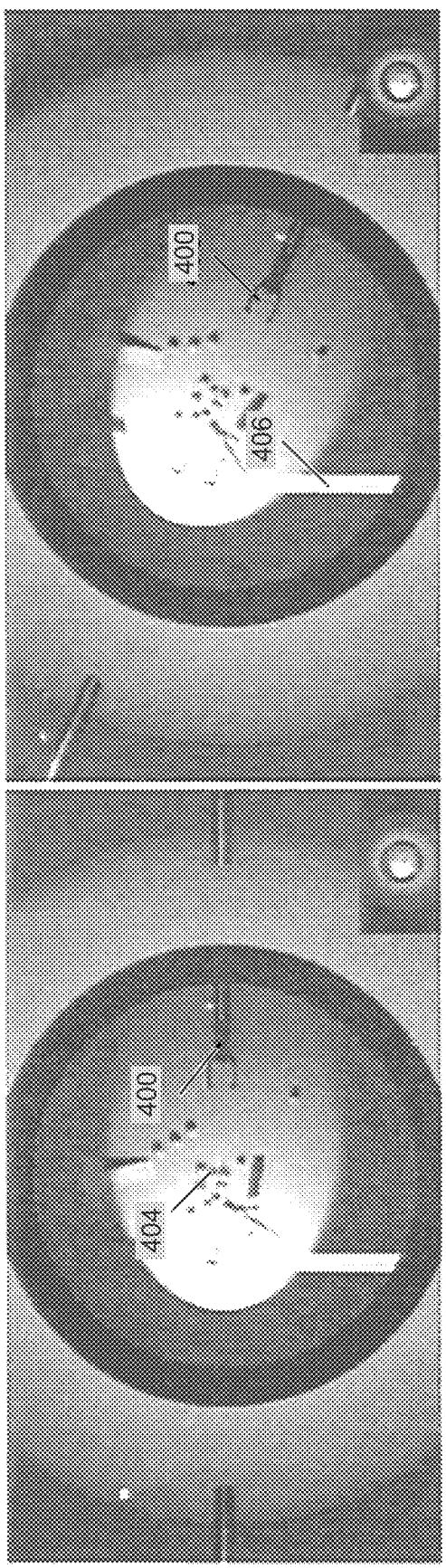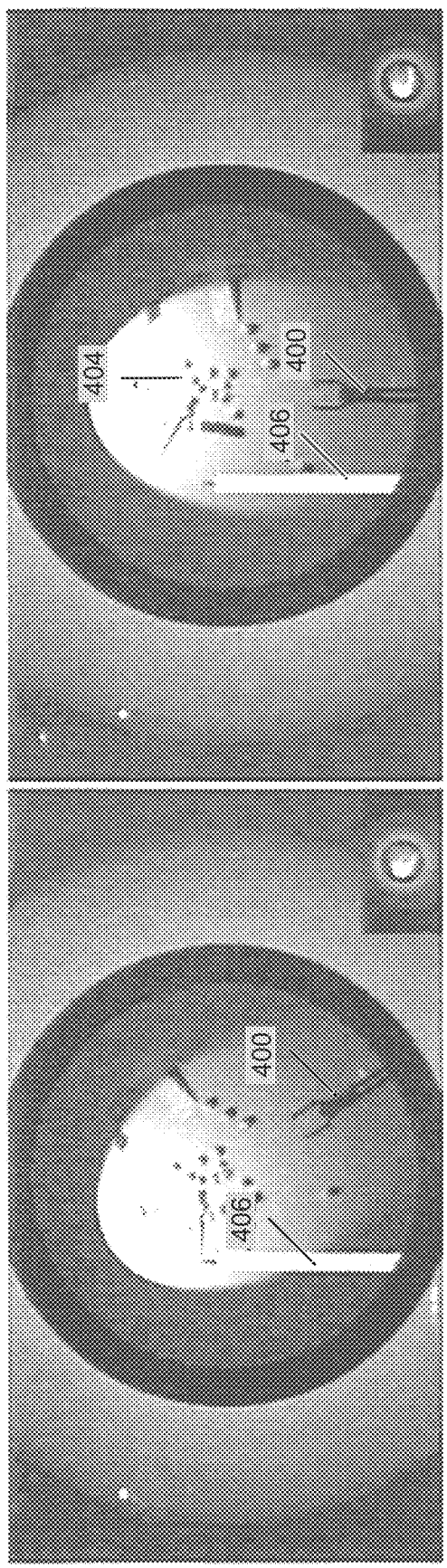
FIG. 5A  FIG. 5B  FIG. 5C  FIG. 5D

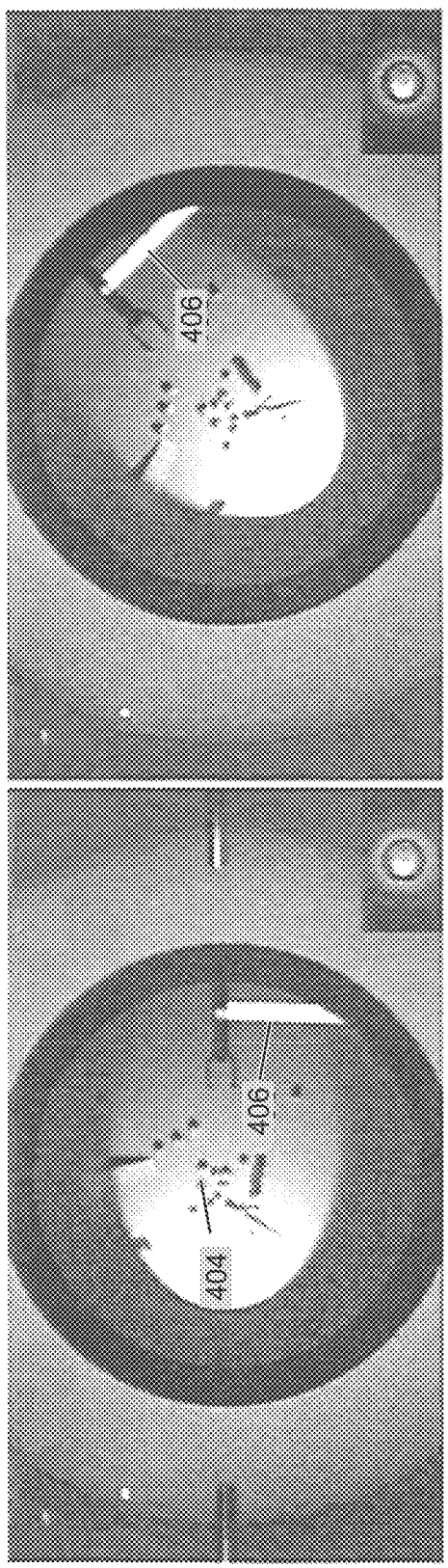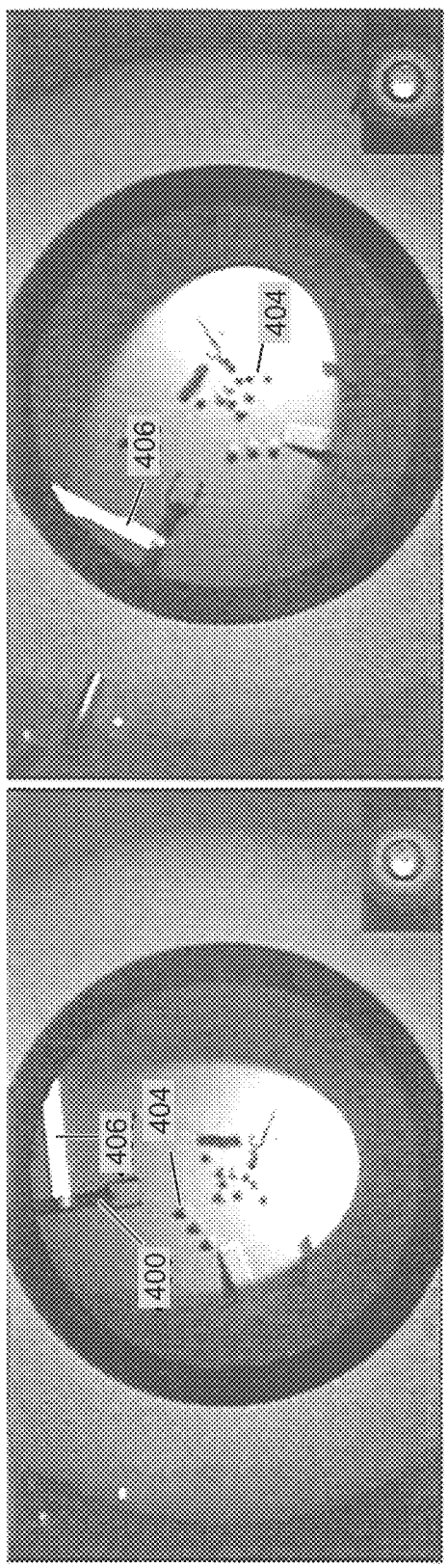
FIG. 6A  FIG. 6B  FIG. 6C  FIG. 6D

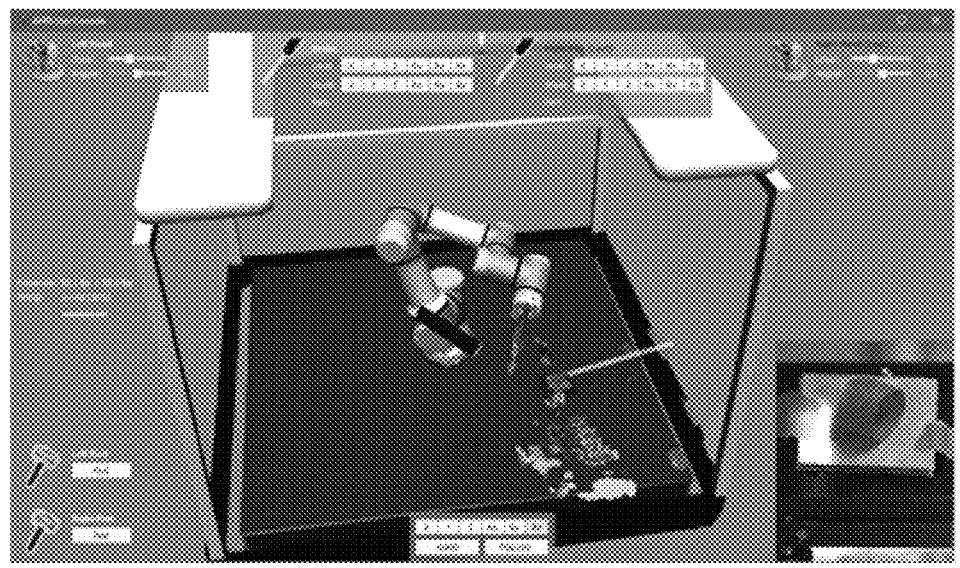
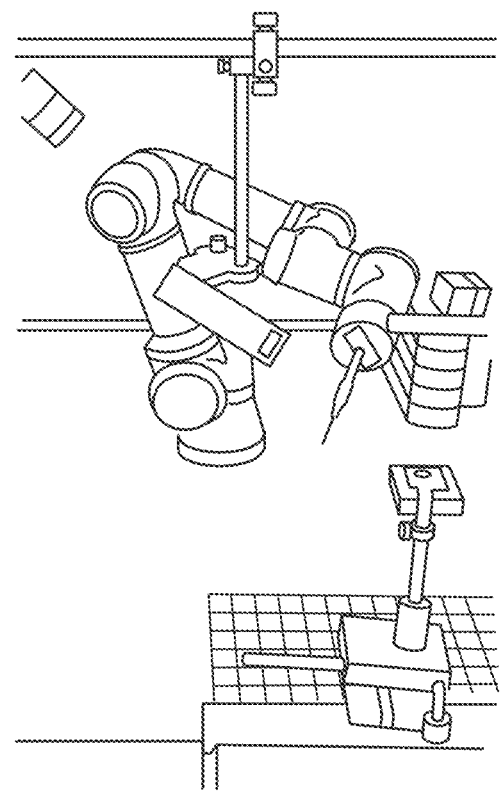
FIG. 21

SYSTEMS AND METHODS FOR ARBITRARY VIEWPOINT ROBOTIC MANIPULATION AND ROBOTIC SURGICAL ASSISTANCE

CROSS REFERENCE TO RELATED APPLICATIONS

This is a 371 national stage patent application of International Patent Application No. PCT/US2016/051360, filed Sep. 12, 2016, and titled SYSTEMS AND METHODS FOR ARBITRARY VIEWPOINT ROBOTIC MANIPULATION AND ROBOTIC SURGICAL ASSISTANCE, which claims the benefit of U.S. Provisional Patent Application No. 62/216,652, filed Sep. 10, 2015 and titled SYSTEMS AND METHODS FOR ARBITRARY VIEWPOINT ROBOTIC MANIPULATION, and U.S. Provisional Patent Application No. 62/366,254, filed Jul. 25, 2016 and titled COOPERATIVE ROBOTIC SURGICAL ASSISTANT AND METHODS OF USING SAME, the disclosures of which are incorporated herein by reference in their entireties.

TECHNICAL FIELD

The present subject matter relates to robotic assistants. More particularly, the present subject matter relates to systems and methods for arbitrary viewpoint robotic manipulation and robotic surgical assistance.

BACKGROUND

Current master-slave robotic surgery systems rely upon visual feedback, either directly via microscope or indirectly via a camera, frequently supplemented with haptics. Visualization is typically at most stereoscopic. Volume-rendered imaging modalities such as magnetic resonance (MR), computed tomography (CT), and three-dimensional (3D) ultrasound, however, can produce 3D surgical field visualizations which invite more flexible visualization and robot control interfaces. With 3D visualization, a surgeon can arbitrarily place their viewpoint in 3D space so as to obtain improved tool or surgical field visualization. In fact, with sufficient imaging resolution and frame rate, the surgeon can rely completely on 3D visualization rather than the microscope or camera in performing surgical tasks. This capability can be particularly useful for optical coherence tomography (OCT) guidance of intraocular microsurgery.

As an example, corneal transplants are one of the most commonly performed allograft procedures. In the United Kingdom, there are approximately 30% more corneal transplants performed yearly than kidney transplants. In the United States, nearly 40,000 full thickness corneal transplants (known medically as penetrating keratoplasty (PKP)) are performed every year.

Despite the success and widespread use of PKP, full thickness corneal transplants are not without drawbacks. There is a risk of rejection which requires chronic, lifetime use of topical steroids with its side effects of glaucoma, cataracts, and infection. There is a risk of graft failure over time which leads many who received their graft before middle age to need a replacement graft later in life. The graft is also held in place by sutures finer than human hair meaning that accidental trauma can rupture the eye, necessitating emergency repair and/or replacement.

As an alternative form of corneal transplantation known as deep anterior lamellar keratoplasty (DALK) which solves most of the aforementioned drawbacks with PKP. In DALK, the only the cornea epithelium and stroma are replaced, leaving the host endothelium intact. The host endothelium is the most cellular and immunogenic layer. Because the endothelium is left in place in DALK, the chance of rejection is zero because a host will not reject its own cells. Also, there is no need for chronic immunosuppression. The endothelium is also the major source of time dependent graft failure; because the endothelium is not traumatized in DALK, graft failure is not accelerated as in PKP. Finally, as a technically "extraocular" procedure, the glove remains intact and is less prone to rupture after trauma.

However, the major barrier to adoption is the technical difficulty in performing DALK. In DALK, the surgeon must remove the top 95% of the cornea (i.e., epithelium and stroma) while leaving the 10-20 μm endothelial layer complex behind. This requires great manual dexterity and experience because depth cannot be assessed directly using the standard ophthalmic surgical microscope. Because of the high level of skill currently required to successfully perform this surgery, very few surgeons are able to perform DALK. Even in experienced hands, the reported perforation rate (i.e., accidentally cutting through endothelium and end the DALK procedure) has been as high as 30%. Accordingly, there is a continuing need for assisting surgeons with performing DALK and other intricate microsurgeries

SUMMARY

Disclosed herein are systems and methods for arbitrary viewpoint robotic manipulation and robotic surgical assistance. According to an aspect, a system includes a robotic tool interface configured to control a robotic tool. The system also includes one or more controllers configured to receive an image dataset of an actual environment within which the robotic tool is positioned. The controller(s) are also configured to generate a virtual environment of the actual environment based on the image dataset. Further, the controller(s) can control display of the virtual environment including a virtual tool controllable by a user for use to control the robotic tool within the actual environment. The controller(s) are also configured to receive user input for controlling the virtual tool to control the robotic tool. Further, the controller(s) can output a command, based on the received input, to control movement of the robotic tool via the robotic tool interface. The controller(s) are also configured to receive user input for altering a perspective view of display of the virtual environment from a first perspective view to a second perspective view. Further, the controller(s) are configured to maintain orientation of display of the virtual tool with respect to the user during display of the first perspective view and the second perspective view of the virtual environment.

BRIEF DESCRIPTION OF THE DRAWINGS

The foregoing aspects and other features of the present subject matter are explained in the following description, taken in connection with the accompanying drawings, wherein:

FIGS. 5A-5D depict a sequence of simulator views showing a camera rotation compensation using the Wand Stationary in View (1 DoF) mode.

FIGS. 6A-6D depict a sequence of simulator views showing a camera rotation compensation using the Wand Moves with View (1 DoF) mode.

FIG. 21 are images of an example AVRS in accordance with embodiments of the present disclosure.

DETAILED DESCRIPTION

Figure 1A:
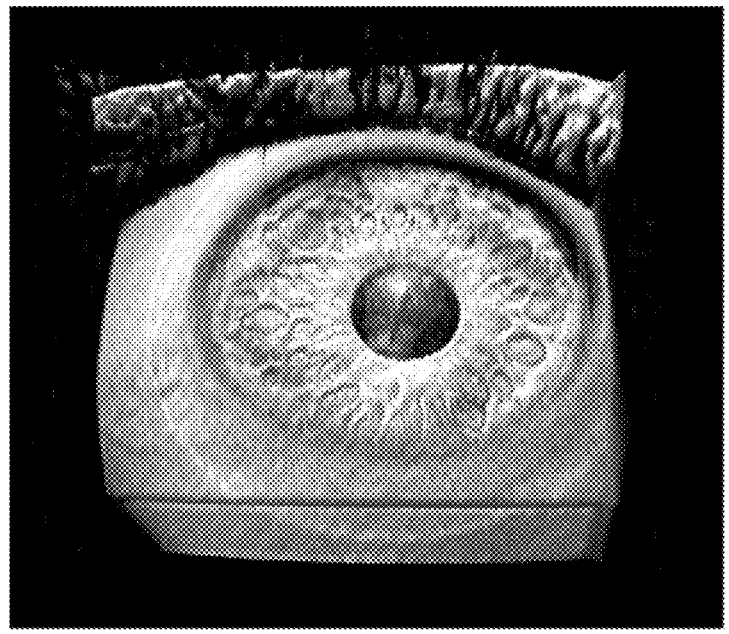
FIG. 1A is an image of an overhead rendering analogous to surgical microscope view.

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 4, 5, 6, 7, 8, 9, 10, 11, 12, 13, 14, 15, 16, 17, 18, 19, 20, 21, 22, 23, 24, 25, 26, 27, 28, 29, 30, 31, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about".

Unless otherwise defined, all technical terms used herein have the same meaning as commonly understood by one of ordinary skill in the art to which this disclosure belongs.

By use of the presently disclosed subject matter, surgeon control input need not originate in a coordinate system identical to that of the operative field. During 3D visualization by use of systems and techniques disclosed herein, the surgeon's input frame can naturally follow the 3D viewport frame to preserve the intuitive relationship between control input and desired robot action. When providing control input, the transformation from the 3D viewport to the surgical frame can be applied such that a robot's actions correspond to the surgeon's intention. Regardless of the input device, the robot control system can derive the goal pose based upon the 3D viewport frame and the surgical frame within predefined safety constraints. For example, while viewing a 3D imaging dataset a surgeon may manipulate an input device which manipulates a surgical tool with a frame of reference which is intuitive for the surgeon such as, but not limited to, near, far, left, and right relative to herself or himself. As an example, if the surgeon rotates the 3D visualization to another viewpoint which either affords her or him a better view of a structure of interest or provides a more comfortable or intuitive viewpoint from which to manipulate a desired tool or tissue interaction, the surgeon's reference frame (e.g., near, far, left, or right relative to the surgeon) can be preserved and needed or desired spatial transforms performed by the robot. This type of interface can be very advantageous over an input device that simply replicates the robot's degrees of freedom.

The present disclosure provides view compensation systems and techniques that can allow surgeon control input to originate in a coordinate system different than that of the operative field. During surgery, a surgeon's input frame may be compensated to naturally follow a 3D viewport frame, thus preserving the intuitive relationship between control input and a desired tool motion. When providing control input, the transformation from the 3D viewport to the surgical frame is applied such that the tool's motions correspond to the surgeon's intention. Regardless of the input device, the tool control system can derive the goal pose based upon the 3D viewport and surgical frames within pre-defined safety constraints.

In accordance with embodiments, a control system may be implemented by interposing a robot between a surgeon and a surgical tool. Systems and methods utilizing arbitrary viewpoint robotic manipulation (AVRM) can have a wide range of applications. As disclosed herein, one application is robotic surgery in conjunction with a 3D imaging modality such as ultrasound or OCT. The 3D imaging modality provides the user with the capability to arbitrarily view the surgical field by manipulating the 3D data (e.g., rotation, translation, scaling, and the like). The AVRM implementation compensates for the manipulation so that the surgeon does not become disoriented when performing maneuvers. By extending this with a virtual tool system, the surgeon can operate from an arbitrary viewpoint while maintaining constraints on the physical tool such as a remove center of motion. The virtual tool provides the capability to control multiple physical tools from one haptic input device, although not at the same time.

AVRM may also be utilized for laparoscopic surgery. In this application, tools may be rigidly mounted to a robot and operate on the patient through fixed ports, but the imaging system can be easily maneuvered to view from different vantage points. Each different viewpoint can keep track of the transform from a reference location to correctly update the virtual tool transform. With the correct camera transform, the virtual tool can control physical tools differently based on the current 2D viewpoint. Notably, arbitrary viewpoint robotic manipulation is not limited to robotic surgery. This framework can be applicable to any situation where a robot is controlled remotely and multiple viewpoints of the workspace are available. One example is mobile robots with single or multiple arms. These robots can be sent into locations not suitable for humans (e.g., bomb disposal, space exploration, and disaster zones) but can still be precisely controlled from different viewpoints. These robots can be outfitted with multiple cameras, such as front, rear, and hand cameras, which can provide multiple 2D viewpoints. Cameras not mounted to the robot, such as closed circuit television, can also be used as viewpoints. The operation of the robot arms can change based on the current view of the user and the location of the virtual tool.

In accordance with embodiments, a robotic, surgical assist device which makes use of 3D surgical field visualization using surgical microscope integrated optical coherence tomography (MIOCT). MIOCT can provide real-time, 3D visualization of the surgical field and can allow a surgeon to directly visualize the depth of their instruments in relation to the tissue at micrometer scale. To improve the surgeon's dexterity to match the visualization, a cooperative robotic assist device is provided for partial thickness corneal transplant surgery. One aspect provides a surgical robot assist device that includes a robotic tissue dissector and feedback control software to assist in surgery. Using this device, while the robotic arm compensates for hand tremor, may maintain spatial position of the surgical instrument tip at critical points in surgery, and may execute pre-planned maneuvers at the surgeon's command, while preventing penetration of the corneal endothelium.

Figure 1B:
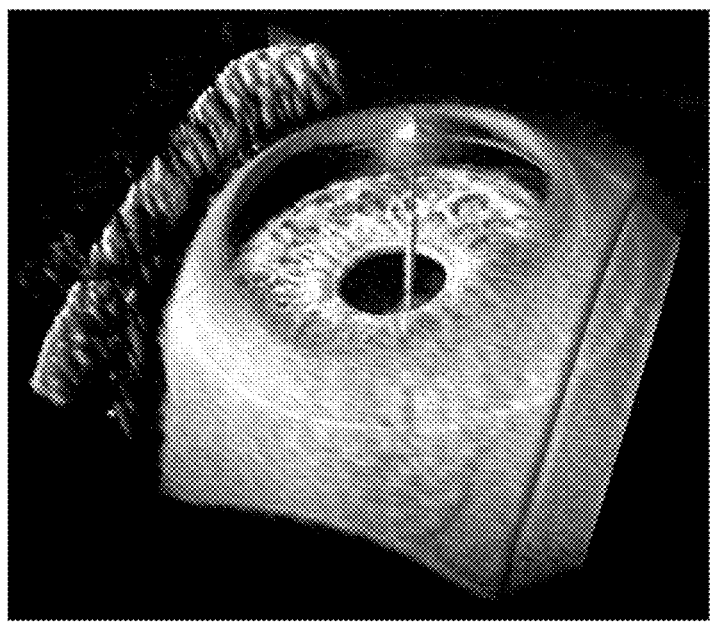
FIG. 1B is an image of a rendering from an angled perspective that reveals the iris's depth with respect to the cornea.

FIGS. 1A and 1B are example 3D OCT images of an eye anterior segment rendered volumetrically. Particularly, FIG. 1A is an overhead rendering analogous to surgical microscope view. FIG. 1B shows rendering from an angled perspective that reveals the iris's depth with respect to the cornea.

As referred to herein, the term "world" is a collection of objects (either physical or virtual) with poses referenced with respect to a given coordinate system origin. AVRM may use three primary worlds.

In an example, a world or actual environment may be referred to herein as the "operating room" which refers to a physical world including a surgeon or other user and input/output devise to or from an AVRM system referenced with respect to the operating room suite. This is the world in which a surgeon generally envisions herself or himself as they operate. Object poses in this world are denoted with the subscript "o".

In another example, a world or actual environment may be referred to herein as the "operative field" which refers to the physical world including a subject or patient and surgical instruments referenced with respect to a target, such as tissue. The operative field world is typically the surgeon's view of target tissue through a laparoscope or surgical instrument. Object poses in this world are denoted with the subscript "f".

In another example, a world may be referred to herein as the "virtual world" or "virtual environment" which includes computer-controlled objects and a camera from which a 3D rendering can be created. The virtual world or virtual environment is not referenced to any physical object. Object poses in this world are denoted with the subscript "v".

As referred to herein, the term "device" or "tool" is an object having a pose in physical space for physical objects and in virtual space for virtual objects. Physical objects or tools poses may be mapped to virtual space via coordinate transformations and vice versa for virtual objects. Thus, devices may have both physical and virtual representations. The AVRM system may use four classes of devices: haptic, wand, tool, and camera.

As referred to herein, a "haptic device" is a physical device or tool operable for input/output to/from an AVRM system. An input device or tool may be any suitable input device, such as a stylus, which a user can move throughout space. An output device or tool may be any suitable output device such as a device (e.g., a stylus) operable to provide force feedback to a user or surgeon. Although a haptic device has a pose in the operating room, the input pose it captures is relative to its base. Thus, the raw haptic input can be expressed in input coordinates specific to each haptic device, which can be represented with the subscript "i".

As referred to herein, a "wand" or "virtual tool" is a virtual representation of a haptic's stylus that exists only in visualization, and we consider hand motions captured by the haptic to directly control the wand rather than the surgical tool, thus decoupling hand and tool motions. This provides a natural way to maintain surgeon orientation during viewpoint changes because the wand moves only in response to hand motions. Viewpoint changes may not affect the wand position because the surgeon's hands remain stationary. The wand concept is fundamental in that it provides an intuitively-connected and perspective-invariant link between the surgeon's hands and the visualization.

Each wand or virtual tool is described by its tip pose W and its pivot P, both in the operating field coordinate system, where P is an axis-aligned pose representing the wand pivot point during camera viewpoint changes. Conceptually, the wand embodies the view transformation V of its haptic input pose H such $$W=VH.$$

During camera motion, the wand records its initial pose W (t0) and initial haptic input H(t0) and updates V.

$$V(t)=P\tilde{D}(t)P^{-1}V(t0)=P\tilde{D}(t)P^{-1}W(t0)H(t0)^{-1}$$

$$W(t)=V(t)H(t)=P\tilde{D}(t)P^{-1}W(t0)(H(t0)^{-1}H(t))$$

The net effect is that the initial wand pose W (t0) is rotated according to the relative camera motion about the axis-aligned pivot pose. Subsequent haptic input H(t) influences the wand relative to W ($t_0$). Thus, the wand moves with the camera about the pivot while responding to haptic input. This corrects hand-tool misalignment.

Although strictly arbitrary, P is most usefully chosen as the camera center point (in the eye-center representation) or the wand tip. If P is chosen as the camera center point and the camera motion is about P, $PD(t)P^{-1}W$ (t0) is the initial wand pose pivoted about P. Thus, subject to haptic motion, the wand will appear stationary on the surgeon's view as desired. Similarly, if P is chosen as the wand tip, $PD(t)P^{-1}W$ ($t_0$) holds the wand tip stationary in the operating field but maintains the wand's orientation as viewed by the surgeon.

As referred to herein, a "tool" is an abstraction of an object, physical or virtual, which the surgeon manipulates via the wand. Physical tools are typically robotically-manipulated surgical tools whereas virtual tools can take many forms, such as representations for virtual fixtures and so forth. In the case of physical tools, the tool pose ultimately drives the setpoint for that tool's physical manipulator.

It is noted that a robotic tool may be moveable by any suitable robot as will be understood by those of skill in the art. Further, a robotic tool interface may be any suitable interface that can be interfaced by one or more controllers or computing devices for operating the robot and thereby controlling movement of an associated robotic tool or tools. The controller(s) and/or computing device(s) may receive user input for controlling the virtual tool to control the robotic tool. Further, the controller(s) and/or computing device(s) may output a command, based on the received input, to control movement of the robotic tool via the robotic tool interface. The controller(s) and/or computing device(s) may receive user input for altering a perspective view of display of the virtual environment from a first perspective view to a second perspective view. Further, the controller(s) and/or computing device(s) may maintain orientation of display of the virtual tool with respect to the user during display of the first perspective view and the second perspective view of the virtual environment. Operation of the controller(s) and/or computing device(s) may be implemented by suitable hardware, software, firmware, or combinations thereof. For example, operation of the controller(s) and/or computing device(s) may be implemented by one or more processors and memory (e.g., instructions residing on the memory that is implemented by one or more processors).

Each tool is described by its tip pose T in the operating field coordinate system. Conceptually, the tool embodies the grab transformation G of its wand input pose W such that T=WG.
The tool tip thus acts as an extension of the wand. Notably, the tool is not directly affected by camera motion like the wand; camera motion influences tool pose through wand input. During a mount operation (next section), the tool records its initial pose T (t0) and initial wand input W (t0) and updates G.

$$G=W(t_0)^{-1}T(t0)$$

$$T(t)=W(t)G=(W(t)W(t_0)^{-1})T(t_0)$$

The net effect is that the initial tool pose T ($t_0$) is affected by the wand's motion from the grab site W ($t_0$).

As referred to herein, "mounting" is the process by which a particular wand is associated with a particular tool. For an AVRM setup with n wands (Wi's) and m tools (Tj's and Gj 's), define the n×m mount matrix M with element mi j such that $$T_j=\Sigma_{i=1}^n m_{ij} W_i G_j$$

with mi j E {0, 1} and $\Sigma^n$ mi j≤1. The mount matrix M thus governs which wands control which tools. The constraints enforce that at most one wand control a given tool at any time. When the surgeon requests that wand Wi control tool Tj, the mount matrix is updated such that mik=δk j and mk j=δki. Control of tool Tj is removed from all wands except wand Wi. When this change occurs, tool Tj records its new grab transformation.

As referred to herein, a "camera" is a virtual device that specifies a user's or surgeon's viewpoint (or vantage pose) from which the surgeon views the operating field. In practice, this is the inverse modelview matrix with which the intraoperative 3D imaging is rendered. Effectively, the camera can define the pose from which the user or surgeon is viewing the virtual world. At the start of a camera viewpoint change, the initial camera vantage pose is recorded at $t_0$. The misalignment at a subsequent time t is $$D(t)=C(t)C(t_0)^{-1}$$

which represents the relative camera motion.

Often, it may be desirable to constrain relative camera motion along or about specific translational or rotational axes, respectively. For example, a surgeon may wish to only compensate camera motion about the vertical axis. In such cases, $\tilde{D}(t)$ is the constrained version of D(t) which effects a zero translation or rotation for the desired axes. For translation constraints, the translation component of D(t) is extracted and the appropriate displacement is zeroed. For rotation constraints, the orientation component of D(t) is extracted as a quaternion and the appropriate quaternion unit coefficients are zeroed. After computing constraints, the translation and orientation components are re-composed to form $\tilde{D}(t)$.

As referred to herein, the term "controller" may refer to the state and logic used for manipulating devices. Each controller may have a pose a mode inputs provided by other controllers or the user. The controller output may be the target pose of its associated device. Additional details are provided herein.

As referred to herein, a "stack" is a set of devices and their controllers operable to work together to perform a single task.

As referred to herein, a "mount" is a mapping that defines how wand motion is coupled to a tool. As an example, this coupling may be a rigid body transformation. When a wand is "mounted" to a tool, the tool's motion is driven by the wand. Additional details are provided herein.

As referred to herein, "intuitively connected" means a connection if two devices if motion of the first device induces motion of the second device that is in accordance with the user's expectations and avoids disorientation of the user. In some cases, this requires that motions of both devices have the same direction.

As referred to herein, "clutching" means the ability to move the haptic stylus without translating the wand position. This can enable the user to access a virtual world workspace much larger than the haptic's physical workspace.

In accordance with embodiments, a virtual tool as disclosed herein can provide a surgeon or other user with the capability to control multiple physical tools from one haptic input device. For example, a surgeon may control physical forceps with the virtual tool to grab and lift a membrane. Once the membrane is in the correct place, the surgeon may "freeze" the forceps in place to thereby decouple the virtual tool from the physical tool. The surgeon may subsequently pick up another physical tool, such as scissors, with the virtual tool to cut the membrane held by the forceps.

Axis alignment and port constraints are utilized in the AVRM framework to improve the surgeon's tool control from arbitrary viewpoints. The axis alignment fixture zeroes the tool translational or rotational motion along specified axes, either in the operating field or local tool coordinate system. This is accomplished using the matrix and quaternion manipulations described further herein. Axis alignment is frequently helpful when aiming the tool shaft (locked world translation) and then advancing the tip (locked local lateral translation and local rotation). The port fixture provides a funnel to guide tool tips through surgical ports and ensures that the tool shaft passes through the port site thereafter. When operating from arbitrary viewpoints, manually maintaining port is impractical because the surgeon no longer directly manipulates the tool. Moreover, automatic port satisfaction frees the surgeon to focus on the tool tip.

Notably, arbitrary viewpoint robotic manipulation is not limited to robotic surgery. This framework is applicable to any situation where a robot is controlled remotely and multiple viewpoints of the workspace are available. The viewpoints do not necessarily need to be represented as 3D data either. Multiple viewpoints represented in two dimensions (2D) may be used as long as the transform between the viewpoints is known.

Figure 2:
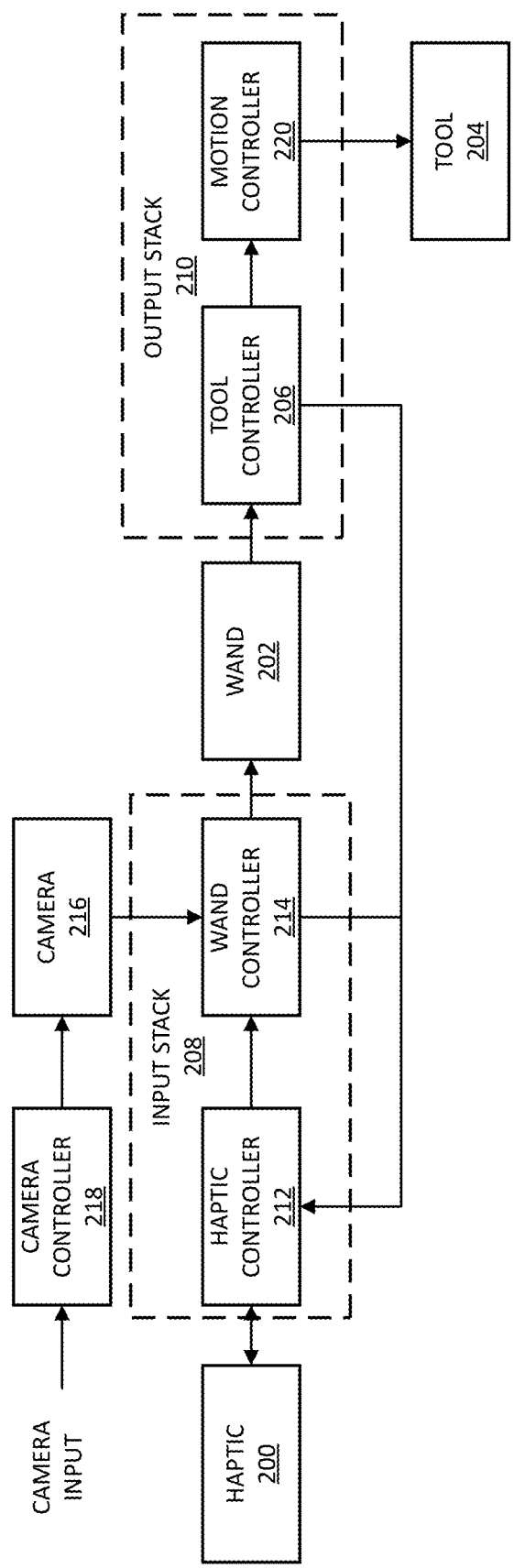
FIG. 2 is a block diagram of an example AVRM system in accordance with embodiments of the present disclosure.

FIG. 2 illustrates a block diagram of an example AVRM system in accordance with embodiments of the present disclosure. Referring to FIG. 2, the system is configured to maintain a user's situational awareness under any view rotation. This includes both slight and radical view changes, such as up-down inversions, and is accomplished by constructing a virtual world in which the user works. The virtual world is frequency an abstraction of the operating field in that live imaging data can be used to build a virtual operating field in the virtual world. The user may interact with this virtual world through haptic devices which provide pose input and force feedback. In FIG. 2, a single haptic device 200 may drive a single wand 202, which may be mounted to a tool 204. It is noted that haptic feedback may be generated by both the wand 202 and tool controllers 206. The dashed boxes indicate components of the input and output stacks (208 and 210, respectively). Each haptic 200 may be associated with an input stack 208 that manages its user interactions. The system produces tool motion as outputs based on user inputs. Each tool 204 may be associated with an output stack that manages its responses to user interactions. FIG. 2 schematically summarizes these components.

Each haptic 200 has an input stack 208 including its haptic controller 212 and a wand controller 214 which act in concert as an AVRM input subsystem. The haptic controller 212 manages clutching operations and properly transforms force feedback from the virtual world to the haptic's input frame as disclosed in further detail herein. The wand controller 214 can manage the wand of the corresponding haptic 200 based on the camera 216 viewpoint and user input via the haptic 200. The camera 216 is operated by a camera controller 218. It is primarily responsible for maintaining the intuitive connection between the haptic stylus and on-screen wand for the user. The techniques through which the intuitive connection is preserved across camera motion are described in further detail herein.

Each tool 204 has an output stack 210 including its tool controller 206 and a motion controller 220 which act in concert as an AVRM output subsystem. The tool controller 206 manages the mounting of its tool 204 with all available wands. It provides candidate mount transforms which are conveyed to the user through both visual and force feedback. Once the tool controller 206 has mounted its tool to a given wand, it drives the motion controller 220 with wand motions. The motion controller 220 is responsible for low-level control of simulated or physical tools such that they track the tool controller's output pose.

Figure 3:
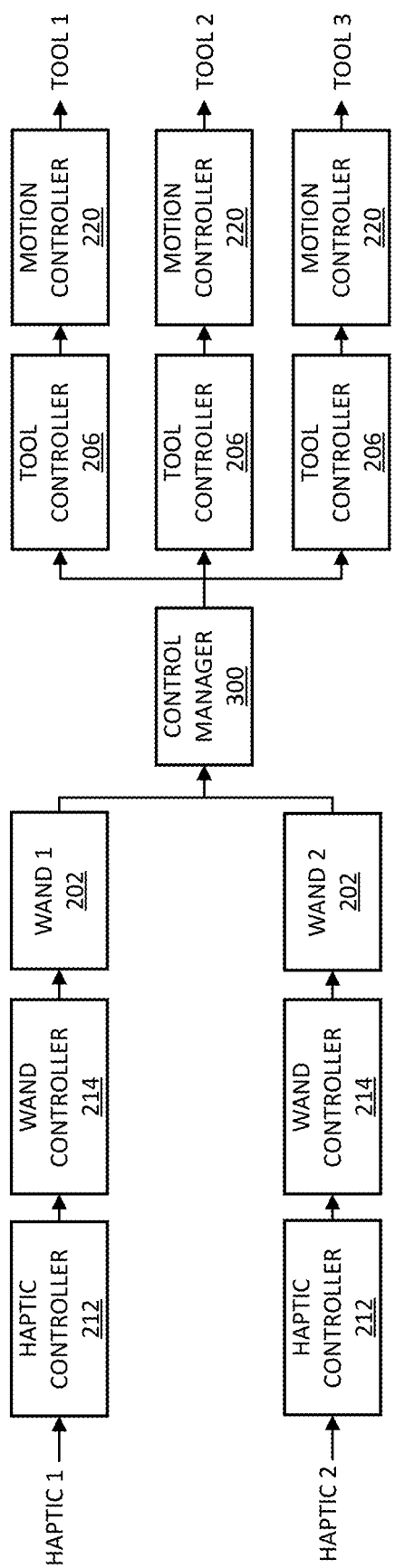
FIG. 3 is a block diagram of a AVRM configuration in accordance with embodiments of the present disclosure.

When more than a single haptic and a single tool are present in the AVRM system, the mounting of tools to wands becomes more complex. In such scenarios, a control manager is introduced between the AVRM input and output stacks such as shown in the example of FIG. 3, which illustrates a block diagram of a AVRM configuration in accordance with embodiments of the present disclosure. Referring to FIG. 3, any number of haptics and wands may be conditionally mounted to an arbitrary number of tools. A control manager 300 may be responsible for determining which wand 202 is mounted to which tool at any given time. It is noted that in FIG. 3 camera and force feedback elements are omitted for clarity. The control manager 300 can connect input stacks to output stacks based on the mounting of wands 202 and tools such that any wand can control any tool. Although FIG. 3 shows only two haptics devices (for the left and right hands), the AVRM control manager 300 may handle any suitable number of haptics. Additionally, the control manager 300 may break wand-tool mounts during camera motions that induce wand and thus tool motions. This is intended to avoid accidentally coupling camera motion to tool motion.

The haptic controller 212 can be configured to transform the haptic stylus pose into the virtual world through a set of operating modes. Further, the haptic controller 212 may provide an abstraction for input devices, may manage haptic feedback, and may implement clutching. The haptic controller 212 may operate with the following homogeneous transformation matrices as inputs and outputs:

$H_i$ denotes the haptic stylus pose in input coordinates received from the device software interface, which includes translational and orientational components $\vec{h}$ and $H_r$, respectively. This coordinate system is aligned with the user's motor frame because the stylus is handheld. The controller assumes that $H_i$ is initially aligned with the virtual world coordinate system as is appropriately scaled for a usable workspace.

$H_v$ denotes the haptic stylus pose in virtual world coordinates and is ultimately an input of the wand controller in the associated input stack. This pose expresses the haptic stylus position in the virtual world coordinates with clutching applied. It is equivalent to the associated wand pose only if no camera motion has occurred.

$X_H$ is the transformation mapping the haptic stylus pose from input to virtual world coordinates. This transformation constitutes the clutching state. If no clutching has occurred, $X_H$=I.

The haptic controller 212 tracks each of these poses/transformations as they vary with time. Whenever a new mode is activated, the controller records the state of each pose/transformation. This time is denoted with $t_g$. The current time is denoted with t.

The Normal mode drives the haptic stylus pose in virtual world coordinates ($H_v$) with prior clutching applied.

$$H_v(t)=X_H(t_g)H_i(t)$$

$X_H$ is held fixed while the mode is operation because clutching is not in progress. This is the default mode.

The Clutching mode can allow the user to translate the physical haptic stylus to a more ergonomic or otherwise advantageous position within affecting the haptic stylus position in the virtual world ($H_v$). Stylus orientation changes are still respected during clutching to maintain the intuitive connection between the stylus and the wand.

Initially, the haptic relative translation input coordinates are computed. The inverse translational offset is applied to $X_H$ to hold the haptic stylus pose fixed in virtual world coordinates.

$$D = \begin{bmatrix} I & \vec{h}(t) - \vec{h}(t_g) \\ \vec{0} & I \end{bmatrix}$$

$$X_H(t) = X_H(t_g)D^{-1}$$

Haptic input rather than haptic virtual world coordinates are used because the user performs the clutching operation in their motor frame, which is aligned with the haptic input frame. Moreover, this ensures that clutching behaves intuitively despite view rotations (e.g., clutching the stylus leftward can permit the user more rightward motion regardless of how the view is oriented).

Then, the haptic pose in virtual world coordinates is updated with the new $X_H$ as in the Normal mode. This ensures that stylus rotations are honored to preserve the intuitive stylus-wand connection while clutching is in progress. Alternatively, a haptic stylus with actuated angular degrees of freedom can be used to lock the stylus's orientation.

$$H_v(t)=X_H(t)H_i$$

The net effect is that wand matches stylus rotations but not translations. This can allow the user to reposition the haptic stylus without affecting its position in the virtual world except for rotations. If the haptic stylus has reached the end of its workspace, the user can enter the clutching mode to move the stylus back within its workspace without moving the wand.

The wand controller is responsible for transforming the haptic stylus pose in virtual world coordinates ($H_v$) into a wand pose in virtual world coordinates while preserving the intuitive connection between the haptic stylus and wand under view rotations. It is implemented with a series of operating modes between which the user may switch seamlessly. The controller operates with the following homogeneous transformation matrices as inputs and outputs.

$C_v$ denotes the camera pose in virtual world coordinates. The camera pose determines the view presented to the user.

$H_v$ denotes the haptic stylus pose in virtual world coordinates received from the associated haptic controller.

$W_v$ denotes the wand pose in virtual world, which is a function of both $H_v$ and $C_v$. It is non-identical to $H_v$ when camera motion has occurred. This output pose is ultimately an input of the tool controller mounted to this wand.

$X_w$ is the transformation between the haptic stylus and wand poses in virtual world coordinates. This transformation is updated as the camera moves to keep the wand intuitively connected to the haptic stylus, a process termed view compensation. This transformation is also referred to as the view compensation state.

The wand controller tracks each of these poses/transformations as they vary with time. Whenever a new mode is activated, the system records the state of each pose/transformation. This time denoted with $t_c$. The current time is denoted with t.

The Disabled mode applies no view compensation such that the wand is driven directly with the haptic stylus pose in virtual world coordinates.

$$W_v(t)=H_v(t)$$

$X_W$ is unaffected in this mode so that view compensation state is not destroyed. This permits restoration of compensation in future mode switches.

$$X_W(t)=X_W(t_g)$$

The net effect is that the user may freely manipulate the wand and camera without any view compensation. This mode is used primarily for assessment of manipulation task difficulty with and without compensation.

The Wand Follows Stylus mode allows the user to freely manipulate the wand with the haptic stylus while view compensation is applied. This is the operating mode when no view rotation is underway, meaning that $X_w$ is constant.

$$X_W(t)=X_W(t_c)$$

$$W_v(t)=X_w(t)H_v(t)=X_W(t_g)H_v(t)$$

The net effect is that the tool and stylus appear intuitively connected despite any prior view rotations because those prior rotations have updated $X_w$ to compensate.

The Wand Stationary in View (1 DoF) mode maintains the intuitive connection between the wand and haptic stylus by moving the wand in the virtual world with the camera during view changes. The connection is thus maintained because the wand appears to remain stationary in the view while the virtual world appears to rotate counter to the view rotation. This eliminates the perception that the view has rotated such that the user remains intuitively connected. Notably, the act of moving the view effectively drags the wand through the virtual world which will also move any mounted tools.

First, the camera's relative transformation in virtual world coordinates is computed. The orientation component is decomposed into rotations about the x, y, and z axes using Euler angle decomposition. The translational offset and the inverse rotation about the z axis are used to drive $W_v$ such that the tool moves with the camera. In actual use, camera translation occurs primarily during camera zoom changes.

$$D = C_v(t)C_v^{-1}(t_g) = \begin{bmatrix} D_x D_y D_z & \vec{d} \\ \vec{0} & 1 \end{bmatrix}$$

$$X_W(t) = \begin{bmatrix} D_z & \vec{d} \\ \vec{0} & 1 \end{bmatrix} W_v(t_g) H_v^{-1}(t)$$

$$W_v(t) = X_w(t) H_v(t) = \begin{bmatrix} D_z & \vec{d} \\ \vec{0} & 1 \end{bmatrix}$$

The intermediate step of updating $X_w$ may be needed because other modes (e.g., Wand Follows Stylus mode) may use $X_w$ to map $H_v$ to $W_v$. If $X_w$ is not updated, future mode switches can cause the tool to jump upon the mode switch and remain disconnected from the haptic stylus thereafter.

The net effect is that the wand remains stationary in the view while the camera rotates. Thus, left and right in the user's motor frame remain aligned with left and right in the on-screen view which maintains the intuitive connection between the stylus and wand.

The Wand Stationary in View (3 DoF) mode is identical to the Wand Stationary in View (1 DoF) mode except that rotations about all axes are compensated.

$$X_w(t) = D W_v(t_g) H_v^{-1}(t)$$

All other aspects of this mode are identical to the Wand Stationary in View (1 DoF) mode.

The Wand Moves with View (1 DoF) mode can maintain the intuitive connection between the wand and haptic stylus without moving the wand in the virtual world. The connection is thus maintained by moving the haptic stylus via force feedback such that it remains connected on-screen with the wand. This can effectively convey the view rotation to the user's motor system by moving their hand with the wand.

First, the camera's relative transformation in virtual world coordinates is computed as in the Wand Stationary in View (1 DoF) mode. The translational offset and the inverse rotation about z are used to compute the $H_v$ that maintains the stylus-wand intuitive connection.

$$D = C_v(t) C_v^{-1}(t_g) = \begin{bmatrix} D_x D_y D_z & \vec{d} \\ \vec{0} & 1 \end{bmatrix}$$

$$H_v(t) = \begin{bmatrix} D_z^{-1} & \vec{d} \\ 0 & 1 \end{bmatrix} H_v(t_g)$$

Next, $X_w$ is updated to hold the wand stationary in the virtual world.

$$X_w(t) = W_v(t_g) H_v^{-1}(t)$$

$$W_v(t) = X_w(t) H_v(t) = W_v(t_g)$$

Note that this update may be needed for the same reason as in the Wand Stationary in View (1 DoF) mode.

Also, the haptic controller may be signaled to provide force feedback to maintain the haptic stylus in the configuration corresponding to $H_v$ (i.e., $X_H^{-1} H_v$). If $X_H^{-1} H_v$ is outside the haptic's workspace, a clutching operation is required. The net effect is that the wand remains stationary in the virtual world and the haptic stylus moves while the camera rotates. The stylus's opposite rotation ($D_z^{-1}$) maintains the intuitive connection with the wand on-screen (i.e., when the camera rotates right, the wand appears to rotate left).

The tool controller can map wand motions to tool motions. The tool controller may be implemented with a series of operating modes between which the user may switch seamlessly. The controller may operate with the following homogeneous transformation matrices as inputs and outputs.

$W_v$ denotes the wand pose in virtual world coordinates, which includes translational and orientational components $\vec{w}$ and $W_R$, respectively. This is received from the connected input stack.

$T_v$ denotes the tool pose in virtual world coordinates. This is the goal pose (or setpoint) which the associated motion controller attempts to achieve. The associated motion controller is responsible for mapping this goal poase in virtual world coordinates to the physical world.

$X_{TW}$ is the transformation mapping the wand pose in virtual world coordinates to the tool pose in virtual world coordinates. This applies world (pre-multiplied) rotations about the wand origin.

$X_{TL}$ is the transformation that permits changing the tool's local coordinate system. This applies local (post-multiplied) offsets and rotations about the wand origin.

The distinct world and local tool transformations grant the tool controller great flexibility in coupling wand and tool motions. The tool controller tracks each of these poses/transformations as they vary with time. Whenever a new mode is activated, the system records the state of each pose/transformation. This time is denoted with $t_c$. The current time is denoted with t. For the below, the first term in each title ("frozen" or "thaw") refers to the tool being inactive or active, respectively, and the second term ("align," "weld," or "track") refers to the relationship between the wand and tool.

The Frozen mode can lock a tool's pose. This mode may be entered when the tool is not mounted to a wand and is a prelude to subsequent thawing.

$$T_v(t) = T_v(t_c)$$

$X_{TW}$ and $X_{TL}$ are unaffected to support future mode changes, most specifically the Thaw Align mode.

$$X_{TW}(t) = X_{TW}(t_c)$$

$$X_{TL}(t) = X_{TL}(t_c)$$

The net effect is that the tool holds its current pose in virtual world coordinates because no wand is mounted.

The Thaw Align mode drives the tool with the wand using the previously recorded world and local tool mounting transforms. This mode is used to restore a previous wand-tool mounting.

$$X_{TW}(t) = X_{TW}(t_c)$$

$$X_{TL}(t) = X_{TL}(t_c)$$

$$T_v(t) = \begin{bmatrix} I & \vec{w} \\ \vec{0} & 1 \end{bmatrix} X_{TW}(t) \begin{bmatrix} W_R & \vec{w} \\ \vec{0} & 1 \end{bmatrix}$$

The net effect is that the previous wand-tool mounting is restored such that the tool moves with the wand in the same manner as before the tool was frozen.

The Thaw Weld mode defines a new wand-tool mounting and drives the tool with that mounting. The weld mount may be such that the relative pose between the wand and tool immediately before the thaw is preserved.

First, $X_{TL}$ is modified to record the mount transform. $X_{TW}$ may be cleared because the entire mount transform is contained within $X_{TL}$.

$$X_{TL}(t) = W_v^{-1}(t_g)T_v(t_g)$$

$$X_{TW}(t) = I$$

This can change the tool's local coordinate system to perform the mount

Subsequently, the tool is driven with the wand as the Thaw Align mode, which reduces to transforming the tool's initial pose with the wand's relative pose.

$$T_v(t) = \begin{bmatrix} I & \vec{w} \\ \vec{0} & 1 \end{bmatrix} X_{TW}(t) \begin{bmatrix} W_R & \vec{0} \\ \vec{0} & 1 \end{bmatrix} X_{TL}(t)$$
$$= W_v(t)W_v^{-1}(t_g)T_v(t_g)$$

The net effect is that the tool behaves as if it is rigidly mounted to the wand. This mode is one way of reconciling wand-tool misalignment following view rotation.

The Thaw Track XYZ mode defines a new wand-tool mounting and drives the tool with that mounting. The track XYZ mount may be such that the tool translates with the wand, but the wand's relative orientation changes are applied relative to the tool's starting pose. This can be advantageous because tool roll, pitch, and yaw are controlled with their original hand (i.e., stylus) motions while the tool's translational motions remain intuitively connected to the wand.

Initially, the wand-tool relative transformation in virtual world coordinates is computed. The orientation component is decomposed into rotations about the x, y, and z axes using Euler angle decomposition. The orientational component about the z axis can be used to produce $X_{TW}$.

$$D = W_v(t_g)^{-1}T_V(t_g) = \begin{bmatrix} D_xD_yD_z & \vec{d} \\ \vec{0} & 1 \end{bmatrix}$$

$$X_{TW}(t) = \begin{bmatrix} D_z & \vec{0} \\ \vec{0} & 1 \end{bmatrix}$$

$$X_{TL}(t) = I$$

The can record a fixed z-axis orientational offset between the wand and tool. This can be advantageous, for example, because most camera view rotations in practice are about the z axis.

The tool may then be drive with the wand as in the Thaw Align mode, which can reduce to driving the tool with a rotated version of the wand pose.

$$T_v(t) = \begin{bmatrix} I & \vec{w} \\ \vec{0} & 1 \end{bmatrix} X_{TW}(t) \begin{bmatrix} W_R & \vec{0} \\ \vec{0} & 1 \end{bmatrix} X_{TL}(t) = \begin{bmatrix} D_zW_R & \vec{w} \\ \vec{0} & 1 \end{bmatrix} \quad (30)$$

The net effect is that the tool behaves as if its position is fixed to the wand while its orientation is still controlled via the stylus. This mode is a second way of reconciling wand-tool misalignment following view rotation.

Another mode is the "Thaw Tip" mode. The Thaw Tip mode can perform a new wand-tool mounting as in the Thaw Weld mode but enforces a zero translational offset. The tip mount is chosen such that the tool tip and wand tip align. This mode is advantageous when the tool is subject to constraints, such as a port constraint as described herein.

$$M = W_b^{-2}(t_h)T_v(t_g) = \begin{bmatrix} M_R & \vec{m} \\ \vec{0} & 1 \end{bmatrix}$$

$$X_{TL}(t) = \begin{bmatrix} M_N & \vec{0} \\ \vec{0} & 1 \end{bmatrix}$$

$$X_{TW}(t) = 1$$

This essentially changes the tool's local coordinate system to perform the mount, but only the orientation is affected. Subsequently, the tool is driven with the wand as in the Thaw Weld mode.

$$T_v(t) = \begin{bmatrix} 1 & \vec{w} \\ \vec{0} & 1 \end{bmatrix} X_{TW}(t) \begin{bmatrix} W_N & \vec{0} \\ \vec{0} & 1 \end{bmatrix}$$
$$= W_v(t)W_v^{-1}(t_v)T_b(t_g)$$

The net effect is that the tool behaves as if its tip is rigidly mounted to the wand tip.

Frequently, it is desirable to constrain tool motion along or about specific translational or rotational axes, respectively. In other circumstances, it is desirable to require the tool shaft to pass through a specific point in space. Axis alignment and port virtual fixtures can be implemented by systems and methods disclosed herein to accommodate these two scenarios.

When an axis alignment constraint is active, it zeroes the tool translational or rotational motion along specified axes, either in the world or local tool coordinate system. For translation constraints, the translation component of Tv(t) is extracted and the appropriate displacement is zeroed. For rotation constraints, the orientation component of Tv(t) is extracted as a quaternion and the appropriate quaternion unit coefficients are zeroed. After computing constraints, the translation and orientation components are re-composed to form $T'_v(t)$. This constrained pose is then used to drive the tool. Axis alignment is frequently helpful when aiming the tool shaft (locked world translation) and then advancing the tip (locked local lateral translation and local rotation).

The port fixture provides a funnel to guide tool tips through ports and ensures that the tool shaft passes through the port site thereafter. When operating from arbitrary viewpoints, manually maintaining port is impractical because the user no longer directly manipulates the tool. Moreover, automatic port satisfaction frees the user to focus on the tool tip. The port definition and constraint rules below enable smooth, automatic passing of tool through ports.

A port is defined by its pose (z axis pointing into port), entry funnel depth $d_i$, "hold" depth $d_h$, and exit funnel depth $d_o$. For a given unconstrained tool pose, d is the z-axis displacement between the port and tool pose. When the tool tip is outside the port (d<0), the ideal tool pose is that pose a distance d along the port's z axis such that the rotation between the tool pose and the ideal pose is minimal. The port constraint linearly interpolates from the tool pose to this ideal pose as the tool tip enters the funnel ($d_h \leq |d| \leq d_h + d_i$). The interpolation ratio increases quadratically with d until the "hold" region when the ratio is unity ($|d| < d_h$). When the tool tip is outside the entry funnel, the interpolation ratio is zero ($|d| > d_h + d_i$).

When the tool tip is inside the port ($d \geq 0$), the ideal tool pose is chosen to pass through the port center. If the port is an angle-priority port, the ideal tool pose is a translational of the tool such that the port is satisfied. If the port is a position-priority port, the ideal tool pose is a rotation of the tool about the tip such that the port is satisfied. As when outside the port, the port constraint linearly interpolates from the tool pose to this ideal pose as the tool tip enters the exit the funnel ($d_h \leq |d| \leq d_h + d_o$). The interpolation ratio increases quadratically with d once the tool tip is beyond the "hold" region when the ratio is unity ($|d| < d_h$). When the tool tip is outside the exit funnel, the interpolation ratio is zero ($|d| > d_h + d_o$).

First, XTL is modified to record only the orientation of the mount transform. XTW is cleared because the entire mount transform is contained within XTL, as in the Thaw Weld mode.

Figure 4:
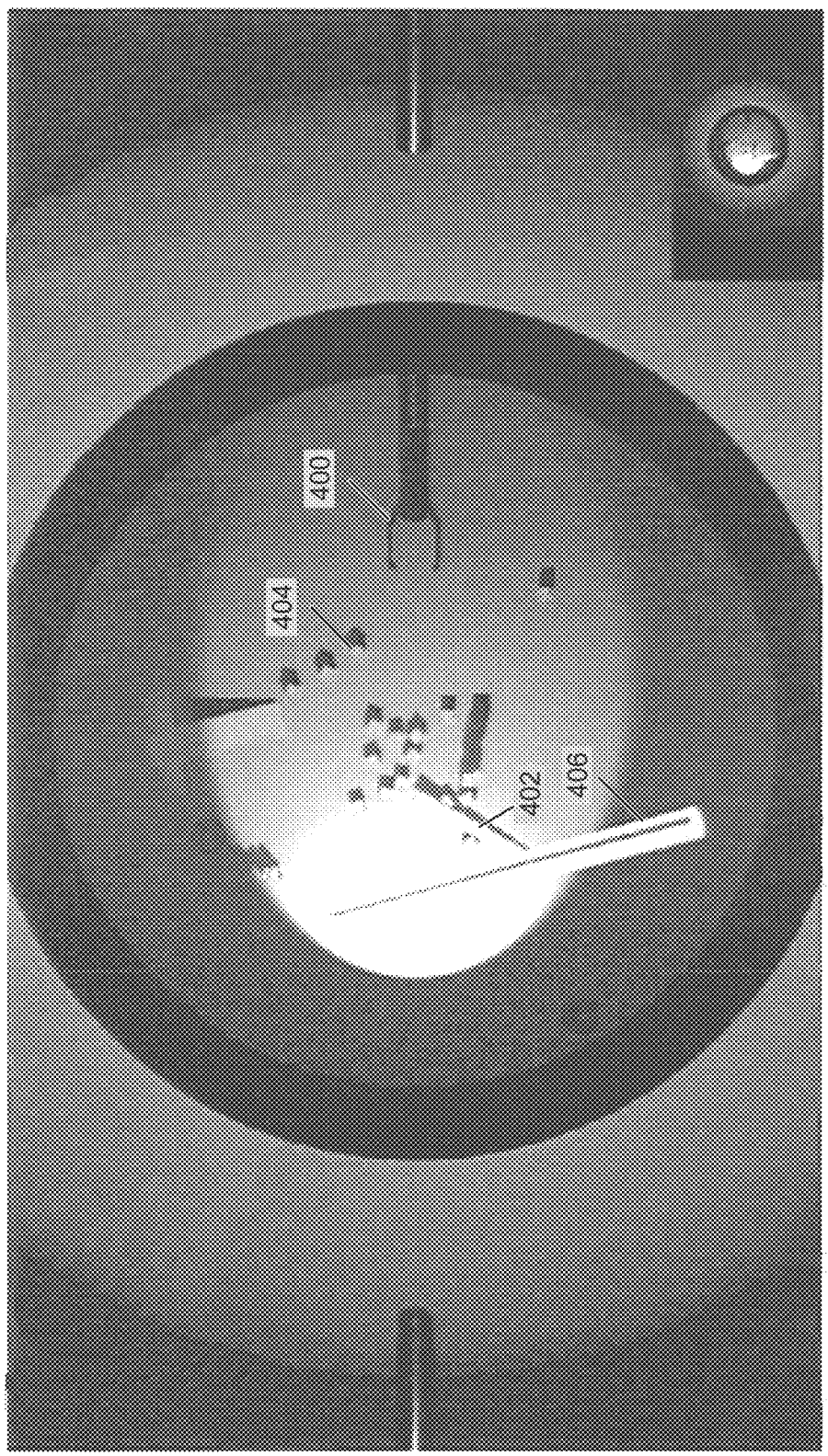
FIG. 4 is a screen display of an example simulator interface in accordance with embodiments of the present disclosure.

For development and prototyping of an AVRM system in accordance with the present disclosure, an eye surgery simulator was developed as shown in FIG. 4. Particularly, FIG. 4 is a screen display of an example simulator interface in accordance with embodiments of the present disclosure. The simulator interface includes two tools (i.e., forceps 400 and light pipe 402) and one haptic viewing the eyeball through the pupil as can be conducted in eye surgery. The eyeball can be seen with a white sclera and a dilated iris. It is noted that the cornea and lens are not shown in the figure. The surgical field includes variously-sized boxes and spheres 404 which can be manipulated with the tools 400 and 402. The forceps 400 are depicted as entering through a port on the right, whereas the light pipe 402 is seen entering through a port on the left to illuminate the operative field. Both tools 400 and 402 are in the Frozen mode and are indicating candidate mount poses with cylinders with red strips for the Thaw Align mode. The wand 406 associated with the single haptic is the cylinder with stripe near the eye's center. Simulator and device statuses are shown in text at the periphery of the screen. An overhead "surgical microscope view" shown in the inset remains fixed in the operating room frame and thus does not rotate with view changes.

The simulator includes a physics engine that can model an eye in an artificial surgical field and can provide virtual surgical tools which interact with the surgical field. The interface can display the state of each haptic and tool controller and can provide a mechanism for mounting wands to tools. Each wand is represented as a translucent white cylinder with a stripe along its shaft as shown in FIG. 4 which moves intuitively with the associated haptic stylus. The camera pose for the virtual world can be independently controlled by the user and can trigger real-time view compensation (see FIGS. 6A-6D). The simulator can support an arbitrary number of wands and tools with its control manager (see FIG. 7).

FIGS. 5A-5D depict a sequence of simulator views showing a camera rotation compensation using the Wand Stationary in View (1 DoF) mode (FIGS. 5A-5D progressively). The wand pose remains fixed in the view while the virtual world, including the surgical field and tools, appears to rotate. After camera rotation, left and right motions of the stylus continue to produce left and right motions of the wand in the rotated view. Of note, the overhead view in the inset shows that the operating field is actually stationary, and it is the wand that rotates. The eyeball is rotating as well although this is difficult to see due to its symmetry.

FIGS. 6A-6D depict a sequence of simulator views showing a camera rotation compensation using the Wand Moves with View (1 DoF) mode (FIGS. 6A-6D progressively). In these figures, the wand remains fixed with the tool while the virtual world, including the surgical field, appears to rotate. Not shown here is that the haptic stylus applies force feedback to keep itself aligned with the wand on-screen. The stylus effectively moves opposite the camera rotation such that the user's motor frame is updated to reflect the view rotation. This keeps the stylus and wand intuitively connected. The overhead view in the inset shows that both the tool and wand remain stationary with the operating field. Once again, the eyeball is rotating as well although this is difficult to see due to its symmetry.

Figure 7:
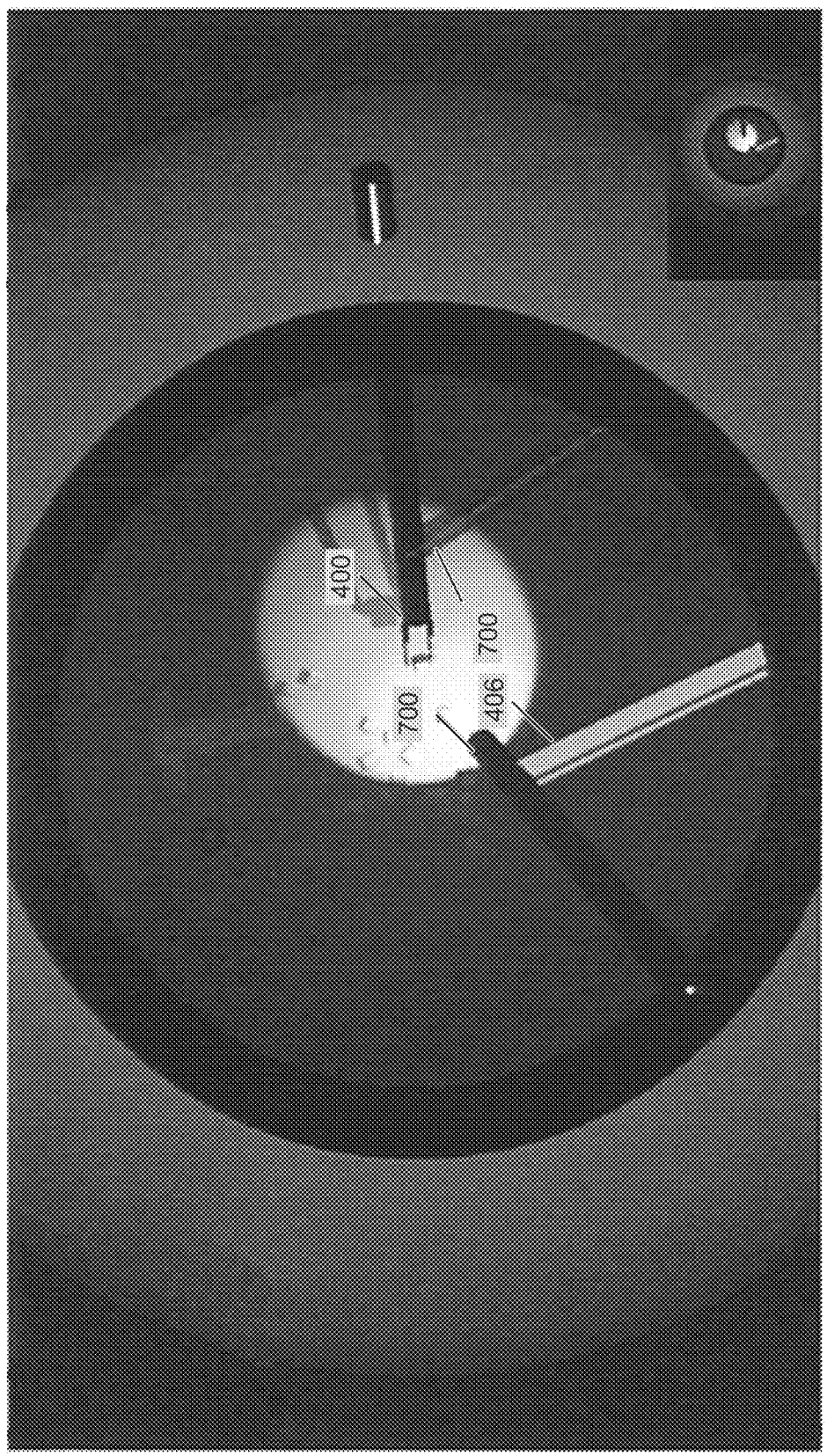
FIG. 7 is a screen display of another example simulator interface in accordance with embodiments of the present disclosure.

FIG. 7 is a screen display of another example simulator interface in accordance with embodiments of the present disclosure. Referring to FIG. 7, the figure shows demonstration of controlling two tools with a single haptic. The forceps are in the Frozen mode holding a simulated object 702 steady and is indicating its last mount with the transparent cylinder 700 with a stripe. The wand 406 is mounted on the light pipe 700 to adjust the operative field illumination. This last mount pose shown for the forceps 400 indicates how the user would need to pose the wand to perform an Align mount. This feature is intended to facilitate restoration of a previous tool mount and can be convenient when the user has dismounted a tool and wishes to remount it.

Figure 8A:
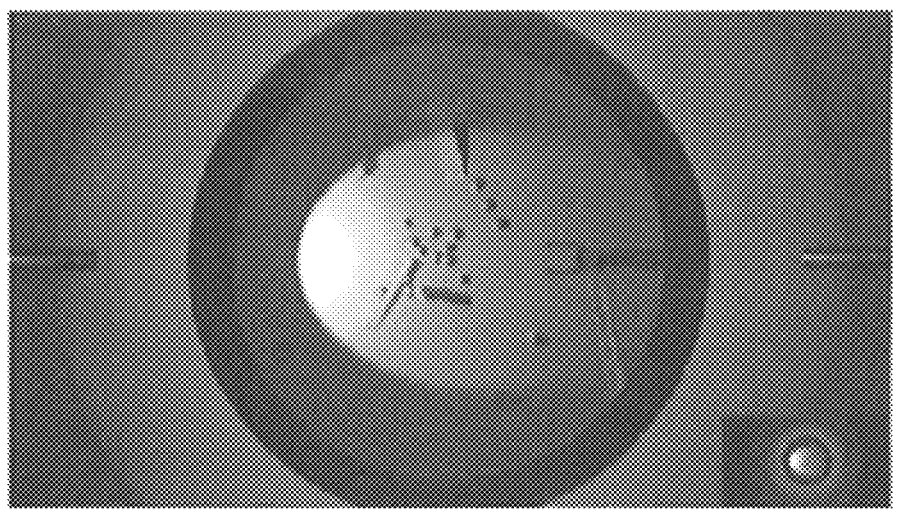
FIGS. 8A-8C depict a sequence of simulator views showing a mounting operation in accordance with embodiments of the present disclosure.
Figure 8B:
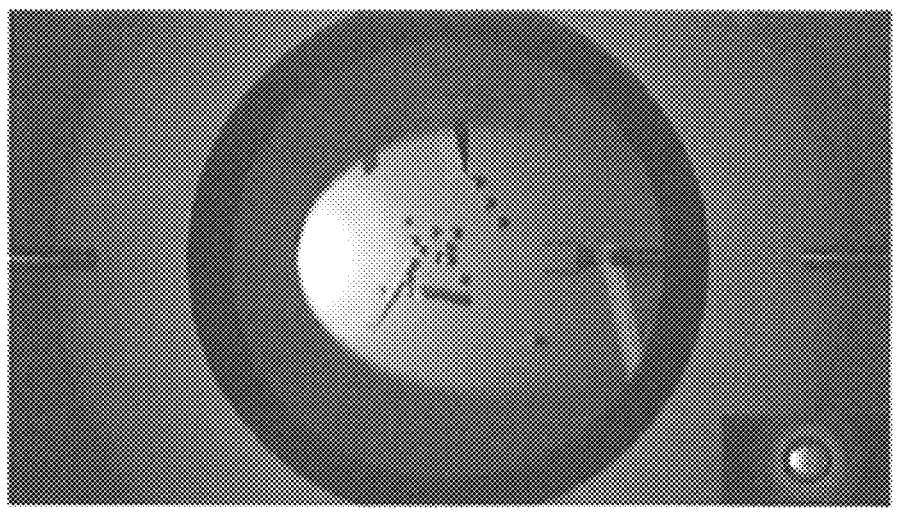
Figure 8C:
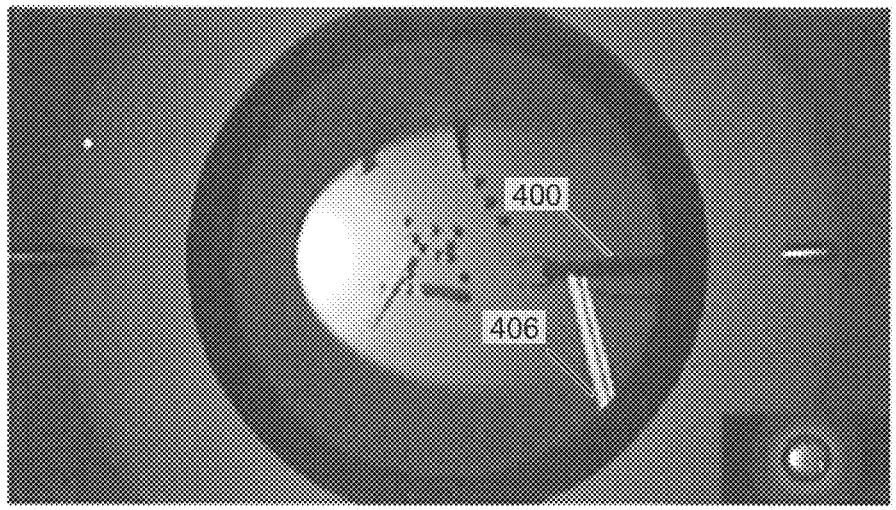

FIGS. 8A-8C depict a sequence of simulator views showing a mounting operation in accordance with embodiments of the present disclosure. Particularly, FIG. 8A shows the scenario of the user having requested a mount, and the haptic is delivering force feedback to snap the wand to the forceps 400. FIG. 8B shows the scenario of the user having achieved a valid mount configuration. FIG. 8C shows the scenario of the user having completed the mount. The forceps 400 can now move in response to wand motions according to the mount type (e.g., a Weld mount in this case).

The attempting to mount the tool to a wand, the interface can provide haptic feedback that snaps the stylus to candidate mount point on the closest tool (see FIG. 8). This candidate mount point is represented as a translucent sphere that changes color when a candidate mount pose is achieved. Any other suitable indicator may be utilized. This can visually indicate the needed wand pose required to perform a mount.

Figure 9A:
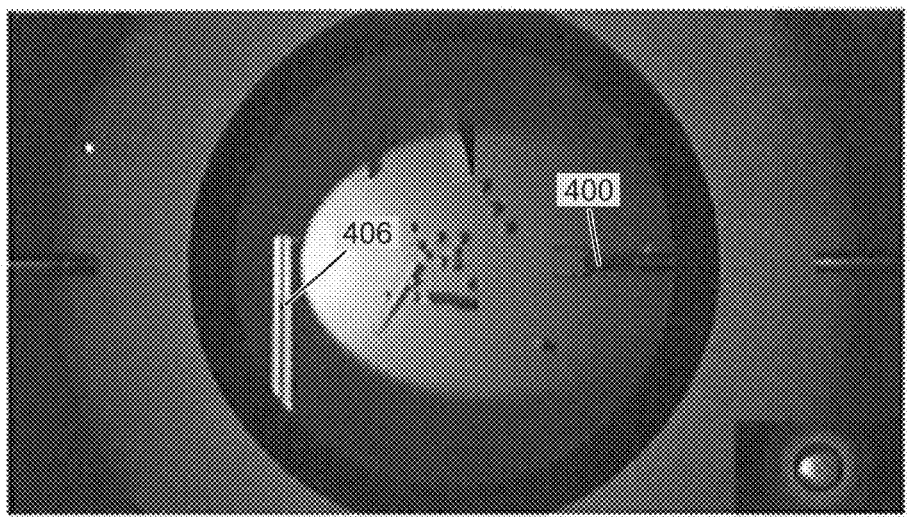
FIGS. 9A-9C demonstrate a clutching operation in accordance with embodiments of the present disclosure.
Figure 9B:
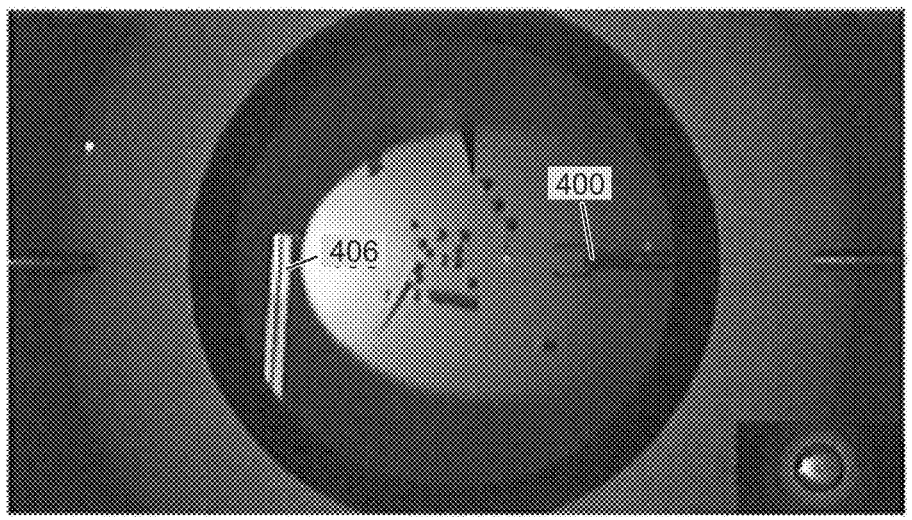
Figure 9C:
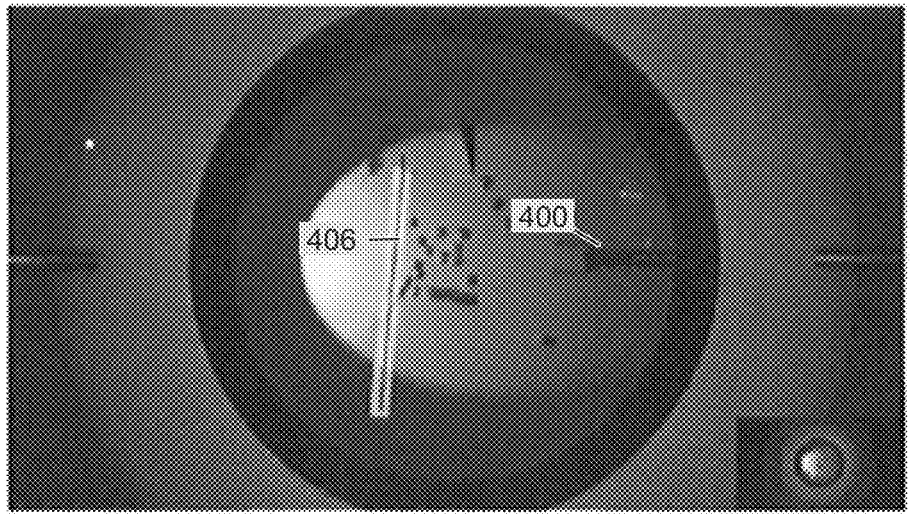

FIGS. 9A-9C demonstrate a clutching operation. More particularly, FIGS. 9A-9C depict a sequence of simulator views showing a haptic clutching operation. It is noted that the presence of the transform axes at the tip of the wand 406. FIG. 9A shows the scenario before the clutching operation. FIG. 9B shows clutching in progress. The wand 406 remain stationary while the haptic input pose ($H_i$) has translated right (new coordinate axes). FIG. 9C shows the scenario after the clutching operation. The wand 406 translates with a fixed offset from the haptic input pose so that the user can better capitalize upon the haptic workspace.

Figure 10A:
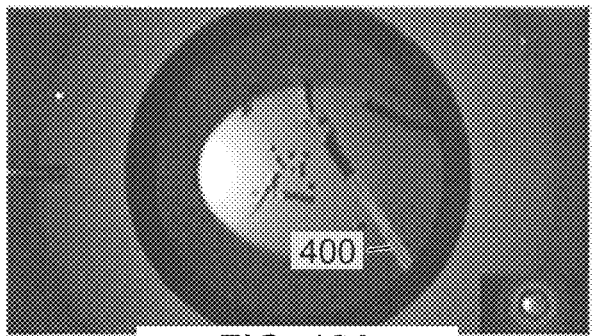
FIGS. 10A-10F are simulator views showing various mount types in accordance with embodiments of the present disclosure.
Figure 10B:
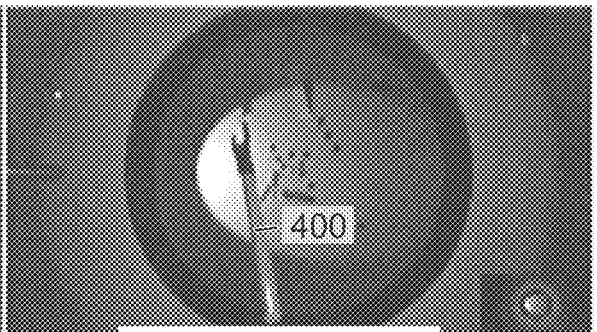
Figure 10C:
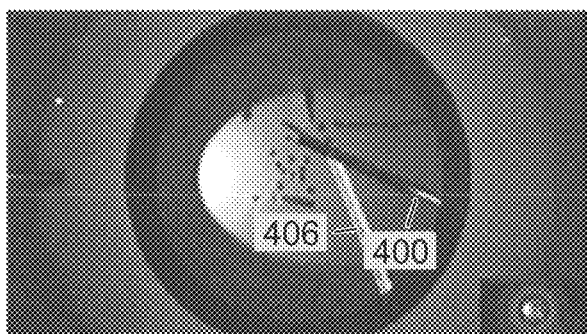
Figure 10D:
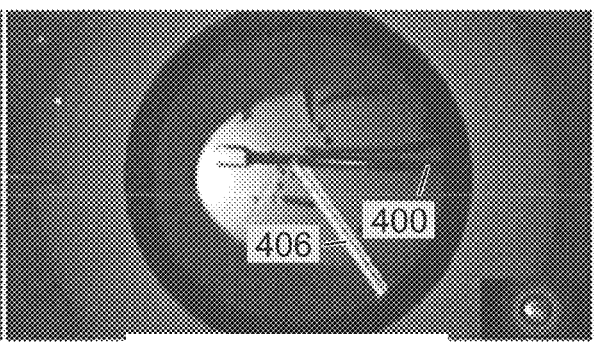
Figure 10E:
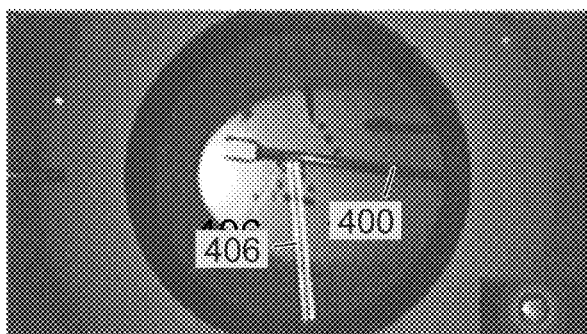
Figure 10F:
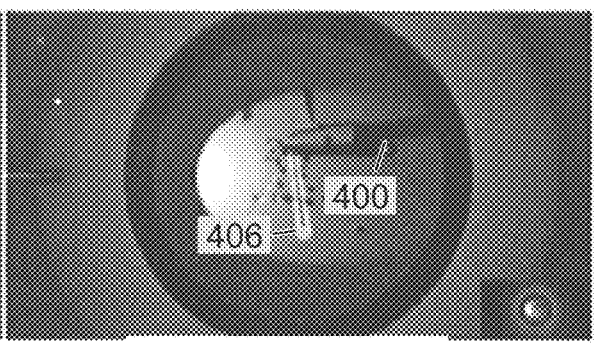

FIGS. 10A-10F are simulator views showing various mount types in accordance with embodiments of the present disclosure. FIGS. 10A and 10B show an align mount. In FIGS. 10A and 10B, the wand and tool shaft remain coaxial throughout the user's maneuver. FIGS. 10C and 10D show a weld mount. In FIGS. 10C and 10D, the tool pivots about the mount point as the user rotates the wand axially. FIGS. 10E-10F show a track XYZ mount. In FIGS. 10E-10F, the tool tracks the mount point translation but still pivots about its local axes.

In accordance with embodiments, virtual reality (VR) based systems may be utilized so that a surgeon can visualize a surgical environment as disclosed herein. A VR system may be used for displaying complex images, including 3D OCT volumes. In addition, for example, a heads-up display (HUD) may be used for providing additional information to a surgeon. In the ophthalmic surgery context, VR and HUD systems can provide surgeons with a heightened situational awareness through careful context-dependent feedthrough of relevant information, such as the patient vital signs monitor or OCT visualizations. Far from "blinded" to the outside world, an HMD-immersed surgeon has access to much more information than they could see through the microscope oculars alone. With increasingly clever VR interfaces that make navigating virtual menus and switching between video displays intuitive, the immersed surgeon can simply look around the operating room as usual while benefitting from OCT and other visualizations.

In accordance with embodiments, a virtual reality pipeline may be implemented using any suitable tools and systems. For example, a virtual reality pipeline in accordance with the present disclosure was implemented using the OpenGL driver (available from Khronos Group of Beaverton, Oreg.) and the OpenVR driver (available from Valve Corporation of Bellevue, Wash.) for an VIVE® immersive virtual reality (VR) system available from HTC Corporation of Taoyuan, Taiwan, or any other suitable VR system. The pipeline has three stages: pose update/prediction, OCT volume render, and compositing. At the start of each OpenVR render frame, the HMD and controller poses may be queried. The pose velocity may be used to predict the next HMD and controller poses at a time when the HMD screen refreshes. These predicted poses may be used to drive the eye view matrices and controller input poses in subsequent stages.

The volume render stage can compute the on-screen volume bounding rectangle and can initiate a ray casting volumetric OCT render within that rectangle using the view and projection matrices for each eye. The bounding rectangle may be computed by projecting the volume's local space bounding rectangular prism onto the eye camera's image plane. The screen space bounding rectangle can be expressed in clip coordinates (UV bounds) for ray casting control along with the view and projection matrices. This optimization can allow the concentration of rays in the OCT screen region while sharing the view and projection matrices with the scene camera. The volumetric render image can consequently remain sharp even when occupying a small screen region. The process can be performed independently for each eye because of the difference in view and projection matrices between eyes. A suitable enhanced ray casting technique may be used to accept an arbitrary projection matrix and clip bounds for volumetric rendering. For subsequent compositing steps, the ray casting output may be converted into an alpha channel of a full intensity OpenGL luminance-alpha texture. The can produce an effect where less dense regions of the OCT volume appear more translucent rather than less bright.

The compositing stage combines the OCT volumetric render image with the 3D scene to produce a final image for each eye. Compositing may be implemented at a suitable oversampling resolution. For simplicity, the VR scene may be divided into a scene background, a scene foreground, and volume layers. The scene background layer may include static models to help orient the user (e.g., a wireframe floor). The volume layer may be an OCT volumetric render image. The scene foreground layer may include interactive models with which the user manipulates the volume (e.g., VIVE® immersive VR system controller models). To build a final image, the scene background may be rendered onto a black background using the eye's view and projection matrix. A completely black or other suitable background may be used to enhance volume visibility. Similarly, an unobtrusive wireframe floor may be used to orient the user without detracting from the volume's visibility. Subsequently, a quad textured with OCT volumetric render image (output of ray casting) in an orthographic projection may be rendered that matches the OCT volume's on-screen bounding rectangle. OpenGl texture linear interpolation may be enabled for upsampling or downsampling the volumetric render image as needed. The scene foreground may also be rendered. These renders into OpenGL framebuffer objects may be performed using an HMD-specific non-visible pixel mask and the resultant textures submitted to OpenVR for HMD presentation.

In accordance with embodiments, an interactive component may be included in a VR OCT volume as disclosed herein to allow a user to translate, rotate, and scale the volume using two VIVE® immersive VR system controllers. The user may engage the translational mode by holding the trigger of one controller only. The controller's translation relative to the start position moves the volume. This can produce an effect where the user grabs and moves the volume by hand. The user may engage the rotational mode by holding the triggers of both controllers. The rotation required to align a line between the controller's start position to a line between their current position rotate the volume. This can produce an effect where the user grabs the volume with two hands and pivots it about its center. The user can engage the scaling mode by pressing the trackpads of both controllers. The ratio of the distance between the controller's current position to the same at their start position scales the volume. This can allow the user to "pull in" or "push away" the volume by moving his or her hands apart or together, respectively.

Figure 11:
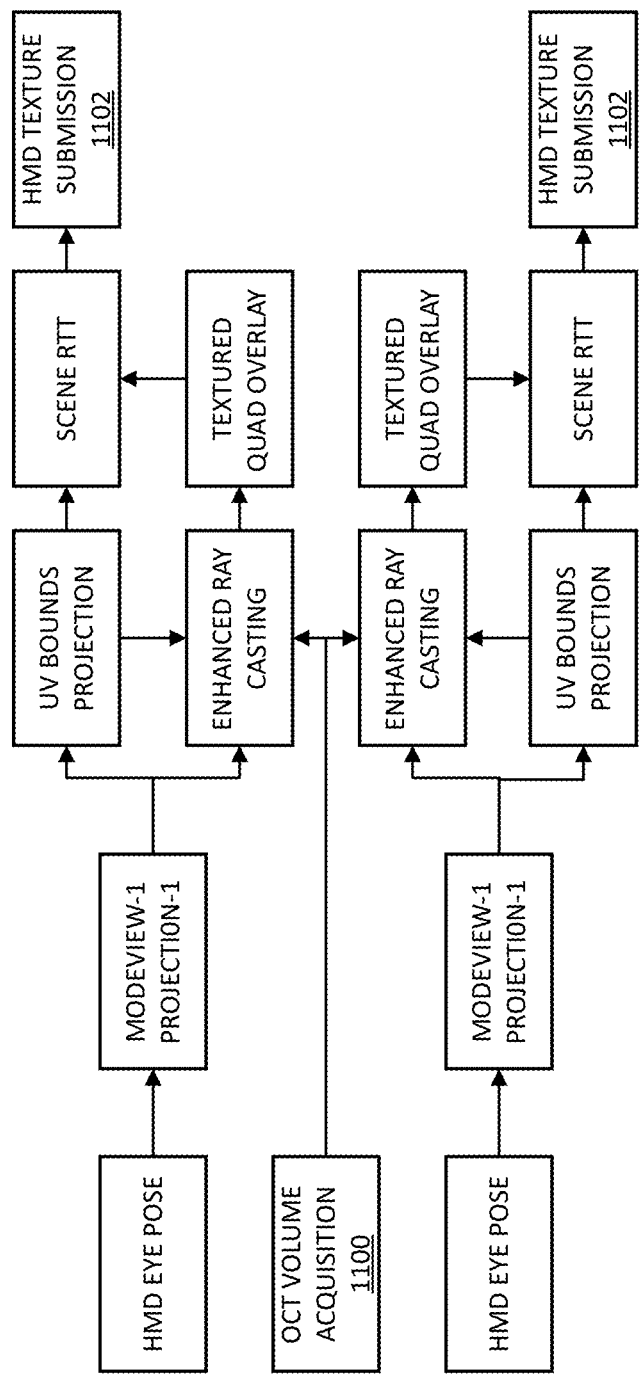
FIG. 11 is a flow chart of an example virtual pipeline overview of the right and left eyes beginning with new OCT volume acquisition or OpenVR frame and completing with HMD texture submissions in accordance with embodiments of the present disclosure.

FIG. 11 illustrates a flow chart of an example virtual pipeline overview of the right and left eyes beginning with new OCT volume acquisition or OpenVR frame and completing with HMD texture submissions in accordance with embodiments of the present disclosure. Referring to FIG. 11, the flow chart includes an overview for right (bottom) and left (top) eyes beginning with an OCT acquisition 100 or OpenVR frame and completing with HMD texture submissions 1102. RTT represents render-to-texture.

Figure 12A:
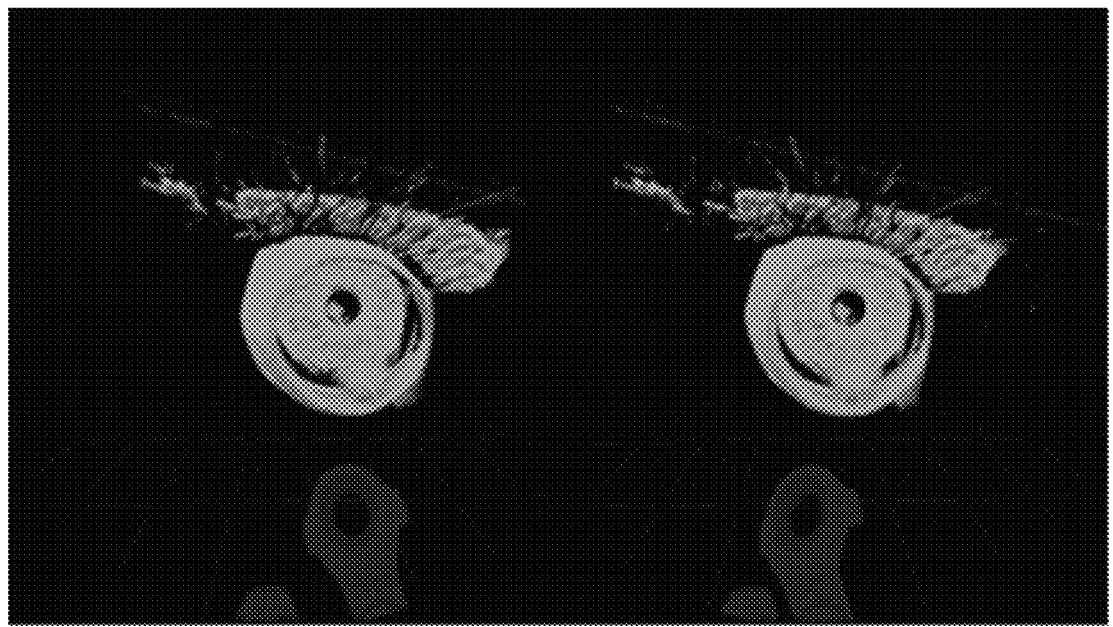
FIG. 12A are images showing left and right views through an example head-mounted display by use of a system in accordance with embodiments of the present disclosure.
Figure 12B:
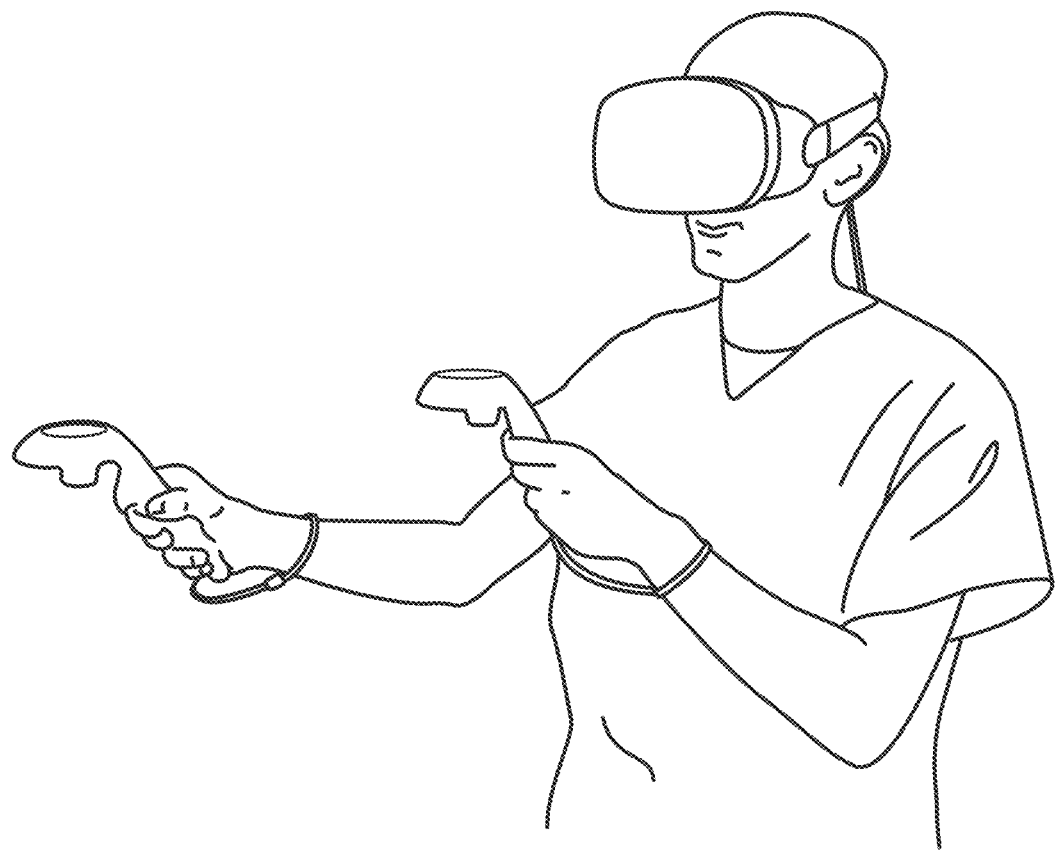
FIG. 12B is an image of a user using the equipment to scale the volume.

FIG. 12A are images showing left and right views through an example head-mounted display by use of a system in accordance with embodiments of the present disclosure. Referring to FIG. 12A, the figure shows an example view through the head-mounted display demonstrating the OCT volume rendering from each eye's perspective without OpenVR's post-processing for distortion and chromatic aberration in the HMD lenses. The VIVE® immersive VR system controller models and wireframe floor are clipped in the corners due to the non-visible pixel mask. FIG. 12B is an image of a user using the equipment to scale the volume.

Figure 13:
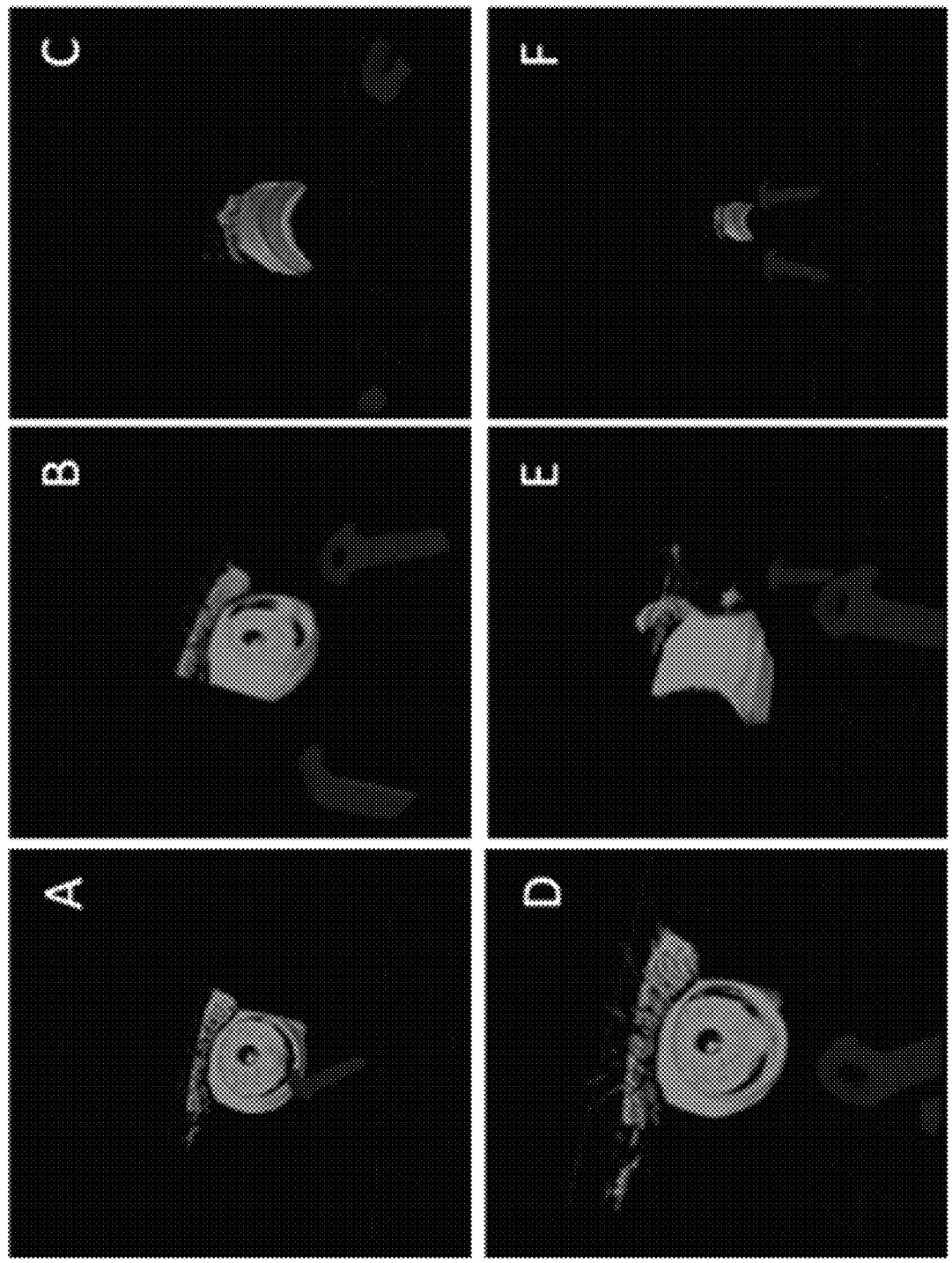
FIG. 13 are images (A-F) showing demonstration of three user interaction modes of a system in accordance with embodiments of the present disclosure.

FIG. 13 are images (A-F) showing demonstration of three user interaction modes of a system in accordance with embodiments of the present disclosure. Referring to FIG. 13, images A→D depict the user pulling a volume closer for inspection using one controller. Images B→D depict a user rotating the volume around the vertical axis by rotating two controllers around each other in the plane parallel to the floor. Images C→F depict the user shrinking the volume by moving the two controllers closer together.

During testing, a rendering pipeline as disclosed herein was evaluated with a static anterior segment Oct volume. The volume was captured with a swept-source OCT system at 512×688×128 voxels using a long-depth sample arm and complex conjugate resolution. Its prominent depth and internal structure are suitable for evaluating VR viewing. Stereo ray casting was performed in a VR pipeline's volume stage at 512×512 pixels which appropriately balanced image quality and performance for this volume.

Figure 14:
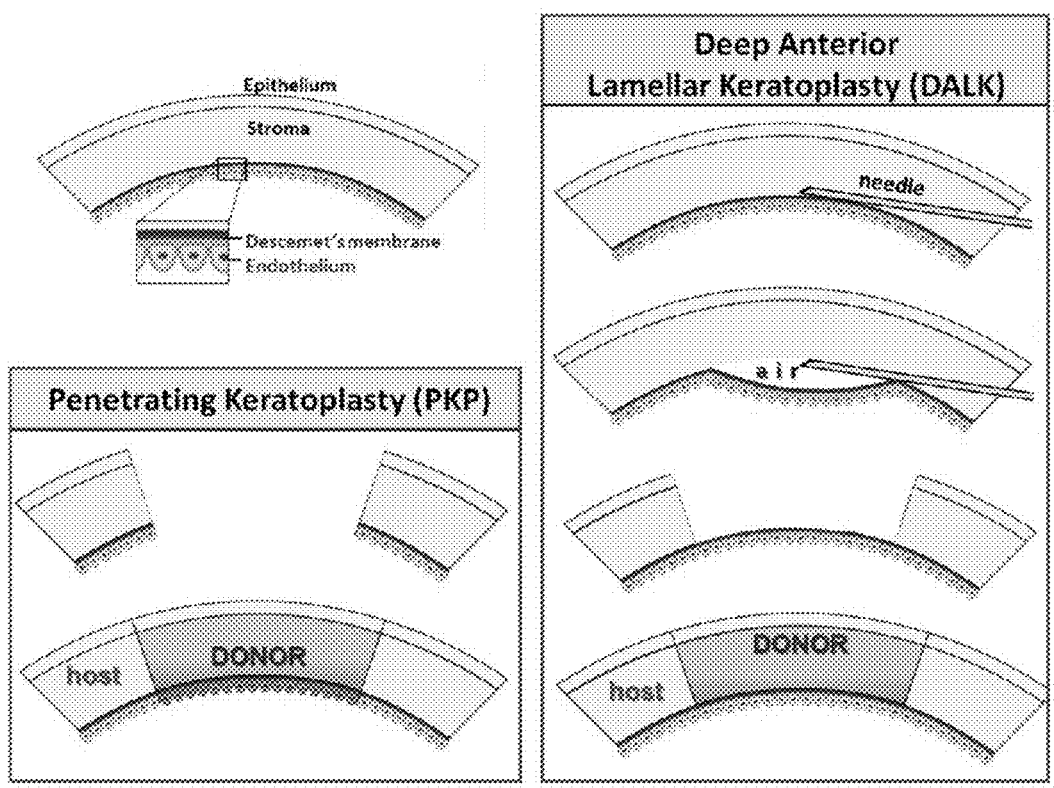
FIG. 14 are images depicting example PKP and partial-thickness DALK corneal transplants.

In an example application, the presently disclosed subject matter may be used for corneal transplant surgeries. Particular types of corneal transplants are PKP and DALK. In DALK, only the cornea epithelium and stromea are replaced, leaving the host endothelium intact. FIG. 14 illustrates images depicting example PKP and partial-thickness DALK corneal transplants. The top left image of FIG. 14 shows the cornea in cross section with layers labeled. Referring to the bottom left image, in PKP all layers of the cornea are punched out and replaced with a donor cornea.

An example of a DALK procedure is shown in the right of FIG. 14. Here, a needle is inserted to pneumo-dissect host Descemet's membrane (DM) and endothelium complex (about 10 μm thick) away from the other top layers. Only the top layers are subsequently replaced. In DALK, the surgeon removes about the top 95% of the cornea (epithelium and stroma) while leaving the 10-20 μm endothelial layer complex behind. The current way of accomplishing this is via the surgical technique referred to as the "Big Bubble" technique. As shown in the right image of FIG. 14, in the Big Bubble technique a need is inserted into the cornea as close as possible to the endothelium, trying to match the posterior corneal curvature without penetrating the endothelium. Air is subsequently injected to pneumo-dissect Descemet's membrane away from the overlying stroma. Inadvertently penetrating the endothelium with the needle can abruptly end the DALK procedure and require that the surgeon convert to the PKP procedure. The Big Bubble technique requires great manual dexterity and experience because needle depth cannot be assessed directly using a standard ophthalmic surgical microscope top-down view, and unpredictable patient motions at this spatial scale are common. Due to the high level of skill currently required to successfully perform this surgery, few surgeons are able to perform DALK. Systems and methods disclosed herein can be utilized for assisting surgeons to successfully perform DALK and other microsurgeries.

In accordance with embodiments of the present disclosure, systems and methods are provided for fast surgical tool segmentation in MIOCT retinal images using a novel height-based tool-tissue classifier using multiple view projections of 3D MIOCT datasets. In an example, the systems and methods are at least partially implemented via software configured to GPU processing. In another example, about 45 ms computation time may be required. In some scenarios, the cornea may be deformed and/or artifactual streaking from reflections may be introduced. These artifacts may be suppressed prior to segmenting the air-epithelium boundary by applying a complex window prior to performing the Fourier transform. An estimate of the needle tip location in the en face view may be computed to select the correct cross sectional scan to segment the boundary of the cornea. The needle tip may be located as the left/right extreme of the needle pixels. Further, the distance to the closest point on the posterior boundary of the cornea may be computed. As a result, real-time identification on the posterior boundary of the cornea and needle positioning monitoring are provided.

Figure 15:
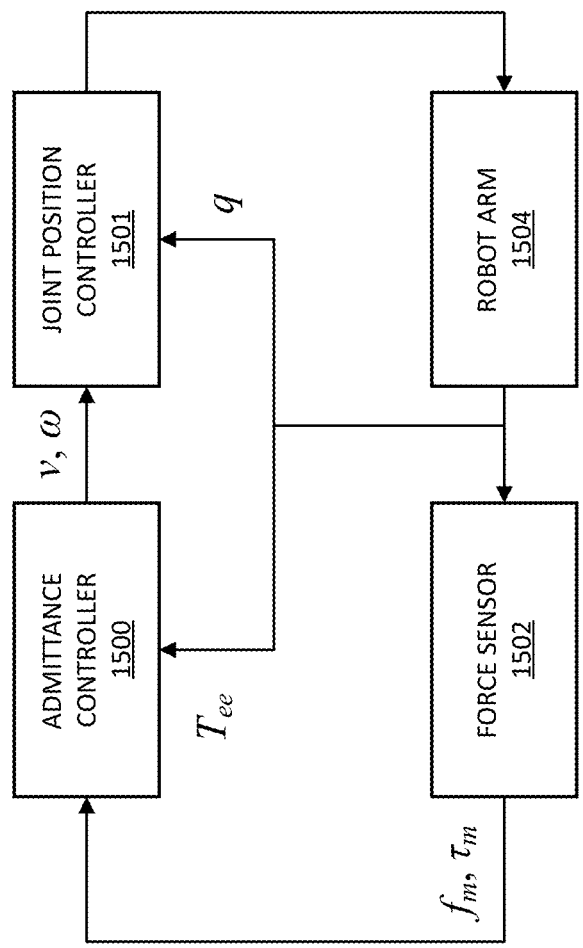
FIG. 15 is a block diagram of an example system architecture for an admittance control scheme in accordance with embodiments of the present disclosure.

FIG. 15 illustrates a block diagram of an example system architecture for an admittance control scheme in accordance with embodiments of the present disclosure. Referring to FIG. 15, an admittance controller can produce a robot end-effector velocity (v, ω) which the robot's internal joint position controller tracks with feedback (q) using joint motor techniques. The force sensor measures external forces ($f_m$, $\tau_m$) dependent on the robot's position ($T_{ee}$) which feeds back into the admittance controller. With admittance control, a normally stiff robot arm that executes a low-level position servo loop can be made to behave as a selectively compliant arm using a higher-level force-based servo loop. This outer force servo loop can cause the robot to exert a desired force on its environment rather than move to a specific position. Using this technique, the surgeon can manipulate a position-controlled robot via a force sensor mounted on its end-effector proximal to the surgical tool. The robot's control system can derive the surgeon's desired tool motion from the measured forces subject to any virtual fixtures in effect, such as a remote center-of-motion, and filtering to remove hand tremor.

Figure 16:
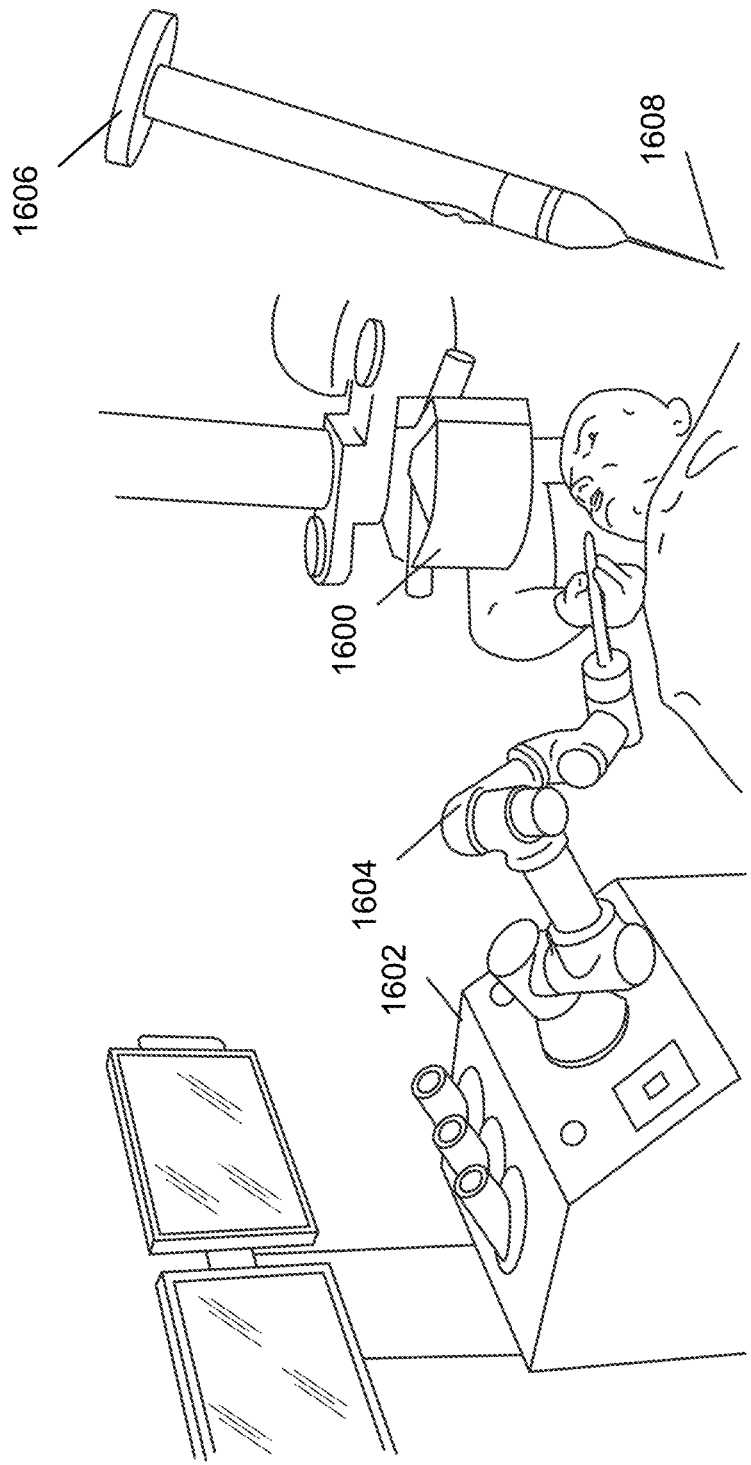
FIG. 16A is an example depiction of a robot-assisted DALK surgical environment in accordance with embodiments of the present disclosure.
FIG. 16B is a perspective view of a DALK tissue dissector handpiece in accordance with embodiments of the present disclosure.

FIG. 16A illustrates an example depiction of a robot-assisted DALK surgical environment in accordance with embodiments of the present disclosure. Referring to FIG. 16A, a surgeon interface 1600 and robot surgical cart 1602 are shown. The cart 1602 includes control interfaces on its front panel (e.g., emergency stop buttons and operating mode displays) and dual monitors for displaying corneal segmentation and planned needle trajectories. The robot arm 1604 can extend from the cart 1602 on the patient's right or left side to maximize its maneuverability for lateral needle positioning and to avoid interference with the operating microscope. The surgeon cooperatively guides the tissue dissector handpiece towards the needle insertion point, and subsequently activates and supervises a pre-planned MIOCT image-guided robotic needle insertion and pneumo-dissection sequence.

FIG. 16B illustrates a perspective view of a DALK tissue dissector handpiece in accordance with embodiments of the present disclosure. The contoured handle can mount to the robot arm endplate 1606 and can terminate in the DALK needle 1608. The handletip, including the needle, is detachable for sterilization or disposal. The handgrip can provide buttons for additional surgeon input and can route plastic tubing to the needle mount for air injection for endothelium pneumo-dissection.

A force sensor can be periodically biased and can respond to gravitational forces as well as surgeon interaction forces. The force sensor readings can be conditioned to implement sensor bias and gravity compensation as follows: $f = T_{ee}(f_m + f_b) - w$ and $\tau = T_{ee}(\tau_m + \tau_b) - T_{ee} r) \times w$ where $T_{ee}$ is the force sensor pose as a homogeneous transformation, r is the displacement from the sensor's measurement point to the tool's center of mass, $f_m$ and $\tau_m$ represent the force and torque measurements respectively, $w = m_a g$ is the tool weight, and $f_b = T_{ee}^{-1} w$ and $\tau_b = r \times f_b$ are bias compensation terms computed when the force sensor bias is performed. Following sensor bias and gravity compensation, low-pass filtering of the resultant force and torque signals are performed to attenuate the surgeon's hand tremor and other measurement noise.

The tool velocity in response to applied forces can follow the dynamics $M_z \dot{v} + B_v = f$ and $I_z \dot{w} + B_\omega \omega = \tau$ where $M_z$ and $I_z$ are the simulated mass and moment of inertia matrices and $B_v$ and $B_\omega$ are the damping matrices (matrices are used for masses and damping to allow different parameters for different directions). These dynamics effectively cause the robot to simulate rigid body motion of the tool handle in a weightless environment with variable moments and damping. The moments and damping may be manipulated according to virtual features suitable for the DALK procedure. For example, as the needle tip approaches the patient's cornea, needle translational resistance may be increased to assist the surgeon in safely contacting the cornea with the needle tip. Additionally, the robot control system can dynamically adjust inertias and damping to ensure stability of the admittance control feedback system by detecting undesired tool oscillations.

To complement fine force sensing using the end-effector's force sensor, control systems and methods disclosed herein can estimate robot joint forces with motor drive currents to detect manipulation of the robot at points other than its end-effector. Given the robot's configuration q, the expected end-effector generalized force is $f_x=[J_{ee}^\tau(q)]^{-1}f_q$ as a consequence of conservation of energy, where $J_{ee}$ is the robot arm Jacobian matrix and $f_q$ are the robot's joint generalized forces (i.e., torques). By comparing the force sensor's measured end-effector force with the expected end-effector force, the application of force to the robot arm proximal to the robot's base can be inferred from the force sensor. The force estimation can be used to enable gross robot arm positioning during setup and cleanup as well as to detect unexpected robot contact with the environment.

In DALK surgical practice, the surgeon typically inserts the needle near the base of the patient's cornea at an oblique angle. Subsequently, after the curvature of the patient's cornea, the surgeon maneuvers the needle to the apex of the cornea where air is injected to separate the endothelium cell layer. In accordance with embodiments, a control algorithm may be implemented that utilizes results of corneal segmentation as disclosed herein for automating this procedure and for co-operatively maneuvering the needle under MIOCT image guidance to a targeted desired endpoint position and orientation within the cornea. To satisfy safety concerns, all forward motion of the needle towards the patient can be initiated by the surgeon; as the needle approaches and enters the cornea, needle trajectory planning can impose increasing constraints on needle motion (such as to limit lateral motion or tremor which can tear adjacent tissue or to avoid corneal penetration).

To maneuver the needle with certain constraints and goals, suitable robot motion planning techniques can be employed. In motion planning, the objective is to move the robot from a start configuration, a position and orientation of the end-effector corresponding to a vector of joint angles, to a goal configuration within robot maneuverability constraints and without colliding with obstacles in the environment. Two example robot planning techniques that may be utilized include probabilistic road maps and rapidly-exploring random trees. These techniques assume a static environment with rigid objects. Broadly speaking, these two techniques randomly sample joint configurations from a set of all possible joint configurations and try to connect the start configuration to a goal configuration via valid (e.g., not in collision) samples. For applications of the presently disclosed subject matter such as a DALK procedure, it is considered that neither the static environment nor rigid object assumptions are true; the eyeball moves as the patient breathes and the cornea deforms as the needle advances.

In accordance with embodiments, the presently disclosed systems and methods can provide a low error metric, the difference between the current needle position and the goal needle position, while obeying constraints, in a closed feedback loop. Shi's method may be utilized by using access to real-time intrasurgical data provided by MIOCT. An example algorithm models the robot dynamics as $\tau(t)=(D(q)+J^T(q)MJ(q))\ddot{r}+(C(q,\dot{q})+J^T(q)MJ(q))r+G(q)+J^T(q)f-K_D s$, where r(t) is the joint torque at time t, q is the robot joint vector, D is the robot inertia matrix, J is the Jacobian matrix of the robot, C are the robot's Coriolis terms, M is the mass of the end-effector, G is the gravity vector, f is the tissue impedance force vector in Cartesian space, $K_D$ is the gain matrix, $s=\dot{q}-r$, and r is the desired bounded velocity minus the error at time t.

Figure 17:
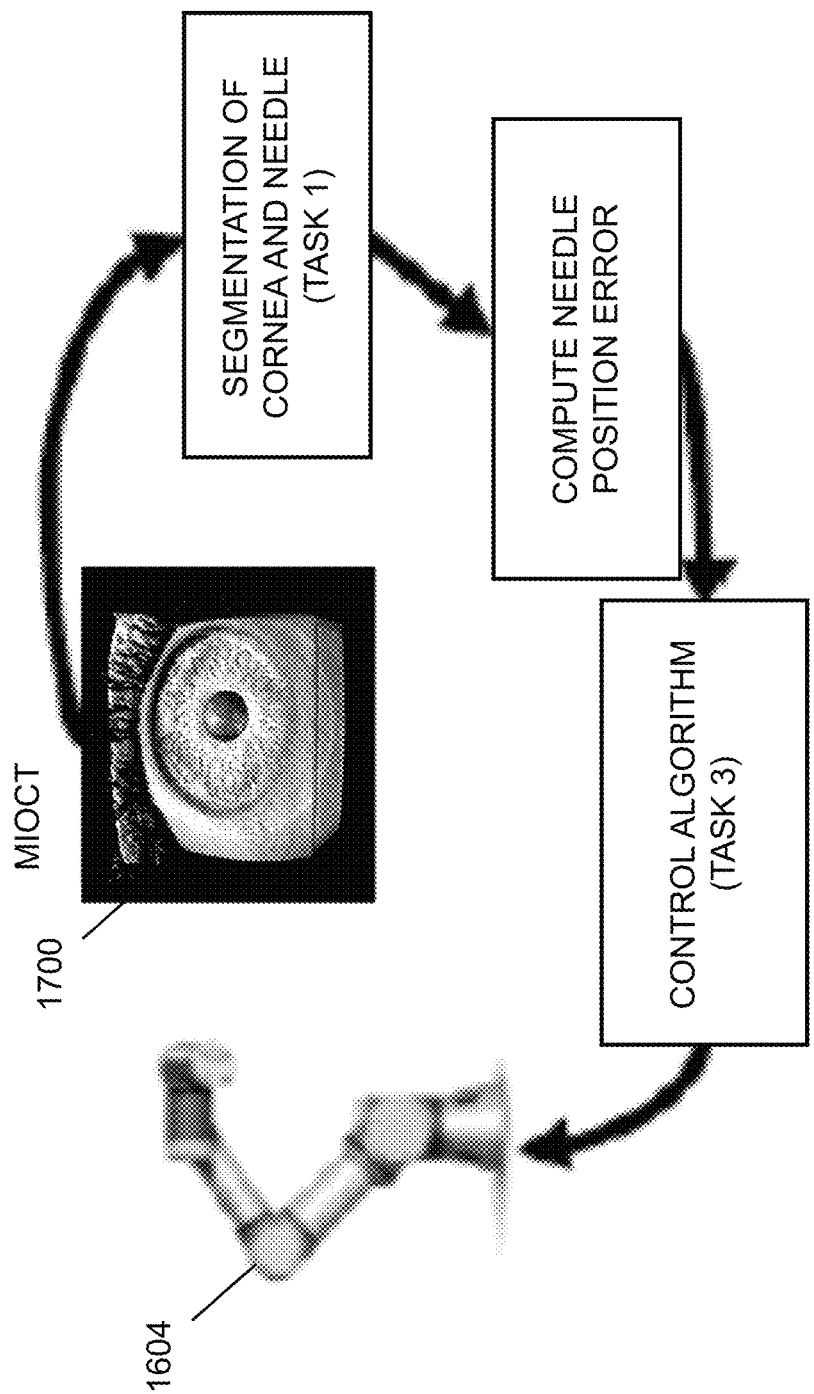
FIG. 17 is a feedback diagram of an example needle control method in accordance with embodiments of the present disclosure.

FIG. 17 illustrates a feedback diagram of an example needle control method in accordance with embodiments of the present disclosure. Referring to FIG. 17, an MIOCT image 1700 of the surgical field is fed into the real time corneal segmentation algorithm, which segments the boundary of the cornea and tracks the needle location in the cornea. The needle location may subsequently be compared to the desired position of the needle to compute the position tracking error. This error may be used as an input to the control algorithm to computer the next robot pose.

To test performance of an implemented DALK robotic assist device in accordance with the present disclosure, an ex vivo model of the DALK procedure was utilized. This model utilized a pressurized artificial anterior chamber (available from Katena Products Inc. of Denville, N.J.) loaded with research-grade donor human cornea from an eye bank. The cornea was then trephined, a 27 gauge needle was inserted into the cornea, and a Big Bubble created.

Figure 18:
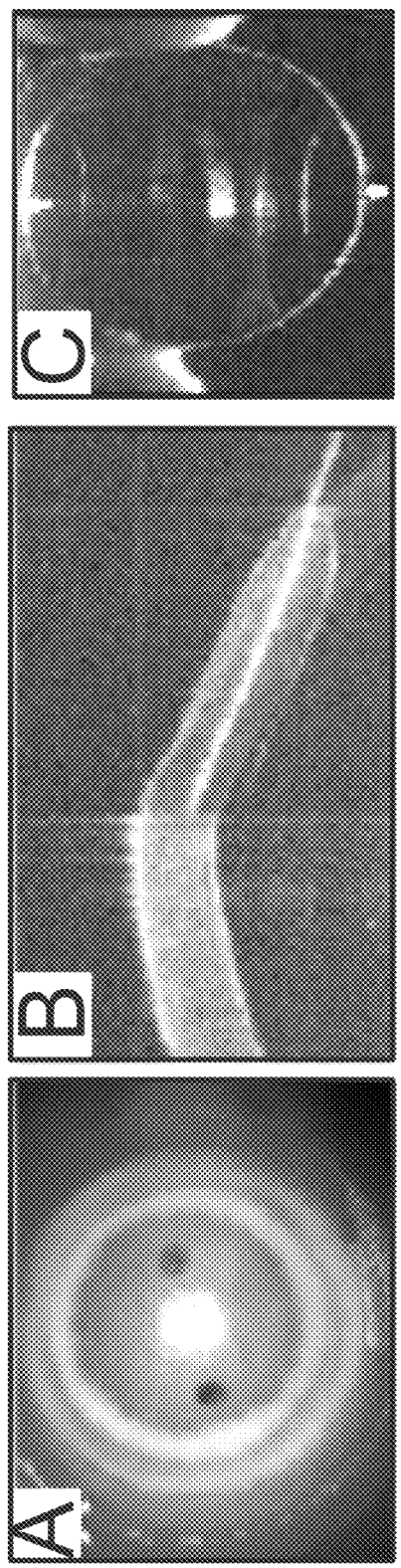
FIG. 18 are various images showing a various views of an ex vivo model of DALK.

FIG. 18 are various images showing a various views of an ex vivo model of DALK. Referring to FIG. 18, image A shows a microscope view of a pressurized human donor cornea loaded in an artificial anterior chamber. Image B shows a cross-sectional OCT view of needle insertion into cornea in an ex vivo model. Image C shows a cross-sectional OCT view of successful Big Bubble pneumo-dissection with clean separation of the posterior corneal stroma from the Descemet's membrane-endothelial complex.

In accordance with embodiments, disclosed herein are bi-manual OCT-guided arbitrary viewpoint systems and methods. A system can transfer viewpoints and tool control modes in a fully operational robotic surgery system. Such systems can be implemented with suitable robot control software and hardware for integrating the system's components, including depth and traditional cameras, an OCT scanner and engine, robotic tool manipulators, and haptic input devices. For software integration, a distributed multi-rate control system can synchronize tasks across multiple computers of different operating systems. For hardware integration, adapters are provided for mounting the robot arms, imaging systems, and surgical tools. The system may include two intuitive user interfaces. One interface can use haptic input devices and 3D monitors/TVs to replicate the seated configuration surgeons encounter in the operating room. Another interface can use immersive virtual reality to allow surgeons to walk through the operative field and manipulate instruments.

An AVRS in accordance with the present disclosure can capture surgeon hand motions with haptic input devices, can display the surgical field visualization using stereoscopic display technology, and can robotically manipulate surgical tools. The 3D visualization system can display both the MIOCT 3D volume from an arbitrary viewpoint and a "wand" for each haptic. A wand is a virtual representation of a haptic's stylus that exists only in visualization, and hand motions captured by the haptic are considered for directly controlling the wand rather than the surgical tool, thus decoupling hand and tool motions. This provides a natural way to maintain surgeon orientation during viewpoint changes because the wand moves only in response to hand motions. Viewpoint changes may not affect the viewed wand position because the surgeon's hands remain stationary. The wand concept is fundamental in that it provides an intuitively-connected and perspective-invariant link between surgeons' hands and the visualization.

Figure 19:
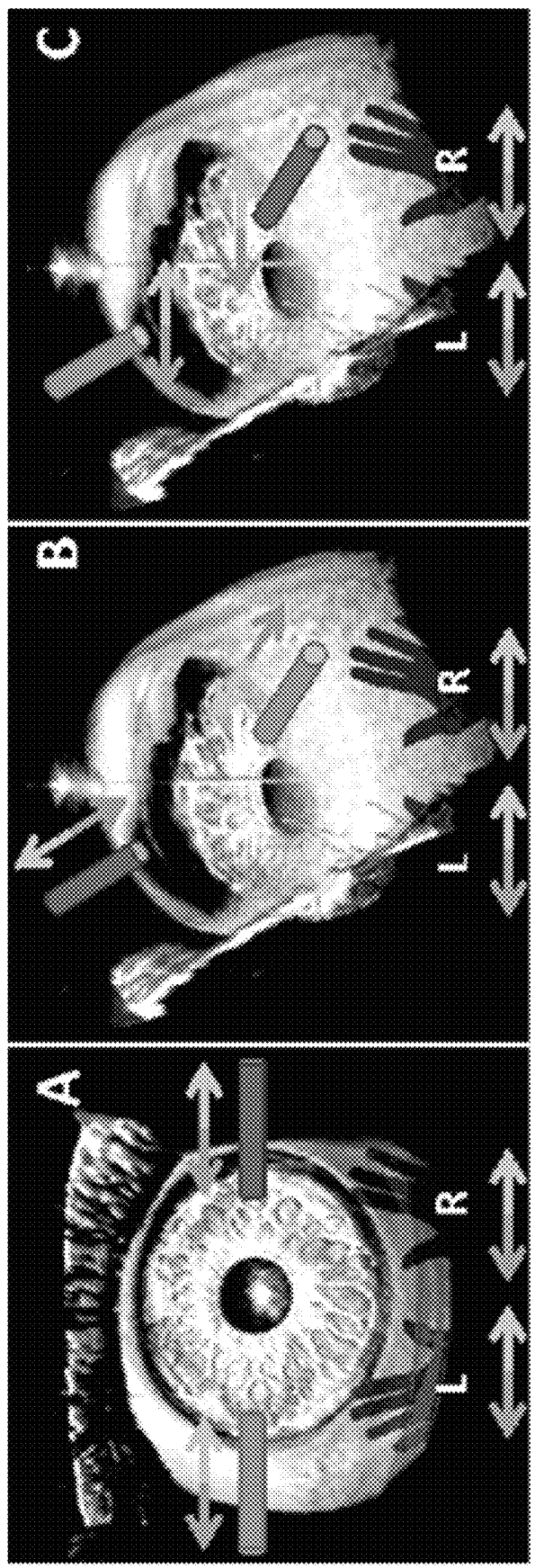
FIG. 19 are images of a view compensation usage case in the anterior segment with two tools controlled with the surgeon's matching hands.

FIG. 19 are images of a view compensation usage case in the anterior segment with two tools controlled with the surgeon's matching hands. Image A in FIG. 19 shows a surgical configuration where left/right hand motions induce left/right tool motions. The surgeon remains oriented because hand and instrument motions are intuitively connected. Image B in FIG. 19 shows a stage after OCT view rotation in a conventional system. In image B, the tools have become misaligned such that left/right hand motions induce non-intuitive angled tool motions. Additionally, the left hand now controls the rightmost tool and vice versa due to a rotation beyond 180° about the vertical axis. The surgeon may consequently become disoriented in this conventional system. Image C shows the results of use of an AVRS system in accordance with embodiments of the present disclosure. In image C, the system has corrected tool motions and, after notifying the surgeon, swapped the tools such that left/right hand motions (now monitored using haptic input devices) induce left/right tool motions (robotically manipulated) of the appropriate tool. The surgeon can thus continue the procedure from the new visualization perspective without interruption or awkward motions and with additional advantages of robotic surgery such as motion minification and tremor removal.

AVRS as disclosed herein has an advantageous mechanism by which wand motions induce tool motions. Most notably, with hand and tool motions completely decoupled, a surgeon's right hand need not control the rightmost tool because notions of left and right lose meaning with the availability of arbitrary perspectives. Surgeons can be allowed to dynamically allow surgeons to choose which wands (i.e., hands) control which tools, switching hands and tools as the procedure or ergonomics demand. In the example of vitreoretinal surgery where tools pass into the posterior segment via ports, the wand tip can be assigned to position the tool tip, and axial wand rotation can be assigned to induce axial tool rotation. Multiple tool manipulation paradigms can be implemented to enhance various surgical maneuvers and facilitate previously ergonomically difficult techniques.

Figure 20:
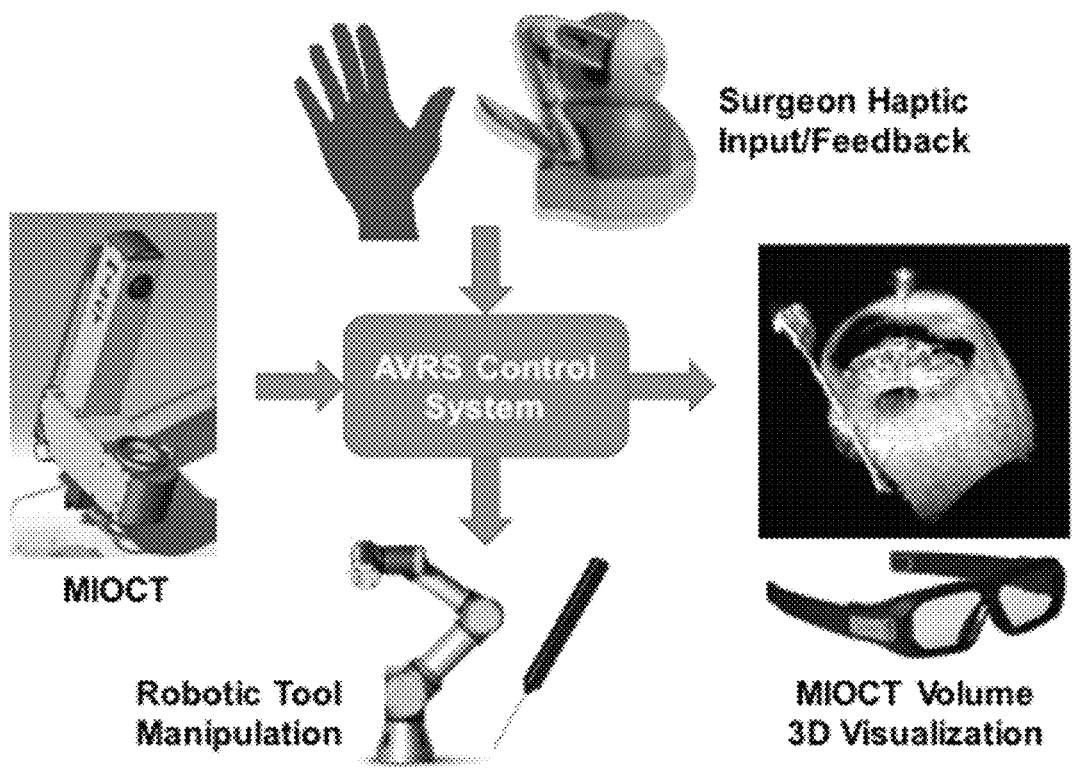
FIG. 20 is a diagram of an AVRS system in accordance with embodiments of the present disclosure.

FIG. 20 illustrates a diagram of an AVRS system in accordance with embodiments of the present disclosure. Referring to FIG. 20, the surgeon's handheld tools and surgical microscope view are replaced with bi-manual haptic input devices and MIOCT operative field visualization. The surgical tools are held and manipulated by two or more robots with micrometer-scale precision. The surgeon's intent is translated into robotic tool motion by the AVRS control system.

FIG. 21 are images of an example AVRS in accordance with embodiments of the present disclosure. The top image shows an example AVRS visualization, whereas corresponding robot setup is shown in the bottom image. The console includes physically accurate robot and environment models, point cloud displays from the depth camera for 3D imaging, the surgical field view (inset in the top image), and a user interface for changing AVRS modes. The surgeon views the surgical field view using a 3D monitor and controls the surgical tool with the haptic input device. The depth camera view can be registered to the world coordinate system using the chessboard target.

Figure 22:
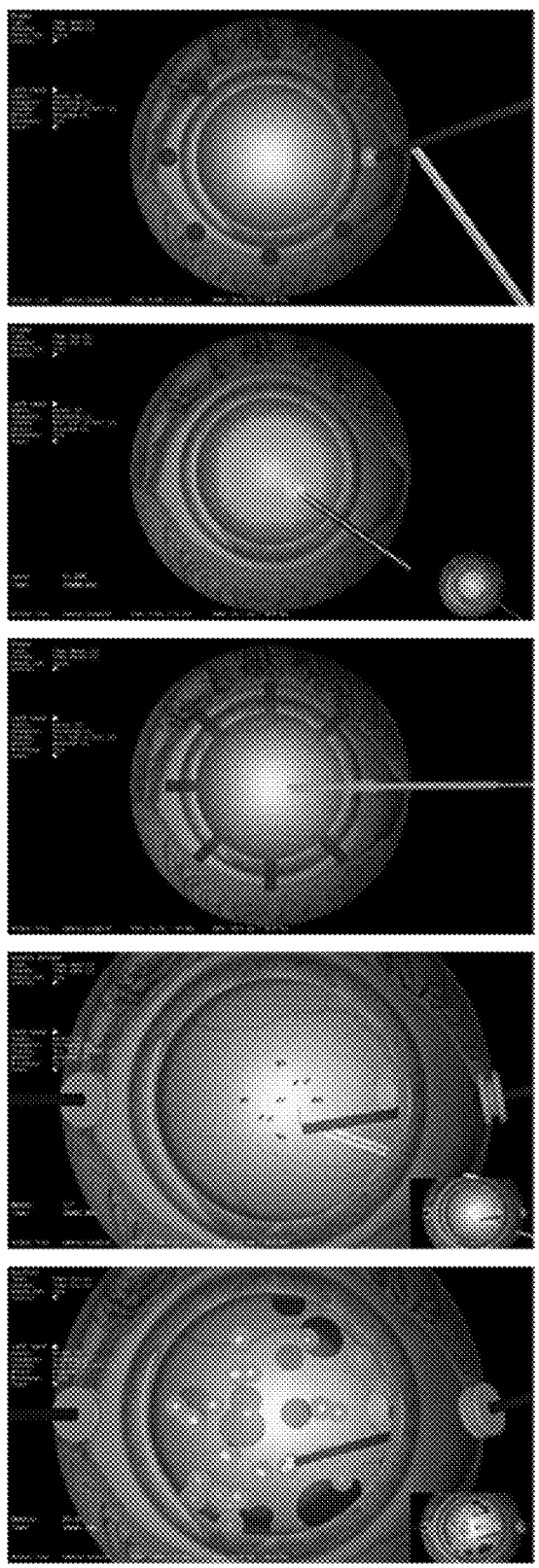
FIG. 22 are images of example AVRS simulator scenarios.

FIG. 22 are images of example AVRS simulator scenarios. Referring to FIG. 22, each scenario is designed for ready adaptation from simulation to physical models. From the top to bottom image of FIG. 22: the top images show Control task positioning the tool tip. The next image downward shows threading needles through beads on the retinal surface to test depth perception and fine tool position and orientation control with scleral port constraints. The third image downward shows suctioning floating debris in the posterior segment to test visualization of peripheral retina with scleral port constraints. The fourth image downward shows lens phacoemulsification to test depth perception and limbal port constrained operation. The fifth image downward shows threading tool through limbal incisions to test fine tool position and orientation control at the eye surface without limbal port constraints.

In accordance with embodiments of the present disclosure, a hypodermic needle inside the cornea and compute the penetration depth into the cornea, the location of the needle may be tracked in three dimensions. These techniques are disclosed as follows, and it should be understood that it may be similarly be applied for tracking any other type of object into a person's body. Three dimensional tracking may be generally broken into two steps: find the needle tip in an en face projection; and segment the cornea and needle at the B-scan where the tip of the tool is located. Because the needle is hyperreflective, a maximum intensity projection (MIP) may be created as the en face view, which can highlight the needle. The MIP may be blurred with a Gaussian filter to denoise the image and perform edge detection with a Sobel filter. Subsequently, a binary image can be generated by thresholding and performing a morphological closing to fill in any holes. The needle is likely to be a large connected component in this binary image, but a large connected component may also be noise, or the reflection of the corneal surface at the apex. To differentiate between tool and other bright reflections, it may be required that the tool's major axis points in a direction that is within five degrees of the direction of the fast scan. The tool may also start near one of the edges of the fast scan direction. These two restrictions may be enforced because inserting the needle parallel to the fast scanning direction of the OCT allows for the best visualization of the needle in the cross sectional scan.

B-scans may be segmented based on the location of the needle tip. The needle is so hyperreflective it can obstruct visualization of the cornea on OCT images. This hyperreflectivity can also introduce horizontal and vertical line artifacts in the images. To reduce the effect of the line artifacts and to better visualize the bottom layer of the cornea, surrounding B-scans may be averaged with the B-scan at the needle tip. From this averaged B-scan, a suitable procedure may be used to segment the top and bottom layers of the cornea. The image may be downsampled in both directions by a factor of two, before calculating three gradient images, two horizontal gradient images and one vertical gradient image. Gradient images are created by convolving the image with [1, 1, 1, 1, 1, 0, −1, −1, −1, −1, −1], [−1, −1, −, 1 −1, −1, 0, 1, 1, 1, 1, 1], and [1; 1; 1; 1; 1; 0; −1; −1; −1; −1; −1] (MATLAB notation) filters. Subsequently, the pixel values may be linearly normalized in these three gradient images to be between 0 and 1. Non-maximum gradient suppression may be performed along each column for the vertical gradient image and each row for the horizontal gradients images using the following equation, $$G_i = \begin{cases} G_i & \text{if } \text{sgn}(G_{i+1} - G_i) - \text{sgn}(G_i - G_{i-1}) < 0 \\ -1 & \text{otherwise} \end{cases},$$

where $G_i$ is the gradient at index i in the column/row. Subsequently, the edge weights between adjacent nodes in the graph may be computed as $$w_{ij} = 2 - (G_i + G_j) + 1e^{-5},$$

where $w_{ij}$ is the edge weight between nodes i and j, $G_i$ is the gradient at node i, and $G_j$ is the gradient at node j. If node j was above node i, the [1, 1, 1, 1, 1, 0, −1, −1, −1, −1, −1] gradient may be used. If node j had the same y-coordinate as node i, then the [1; 1; 1; 1; 1; 0; −1; −1; −1; −1; −1] gradient may be used. If node j was below node i, the [−1, −1, −, 1−1, −1, 0, 1, 1, 1, 1, 1] gradient may be used.

Once the graph is created, layers may be found by using a graph search method. To segment more of the top layer of the cornea, the graph search may be started below the location of the tool. The is found via simple thresholding. After segmenting the top layer, the location of large negative second derivatives (if any) may be found and points removed from the segmented line before/after (depending on which half of the image) before fitting a second order polynomial to the segmented line. We can then combine the $2^{nd}$ order fit with the segmentation, via feathering or where the two curves intersect, to finalize the top layer segmentation.

Figure 23:
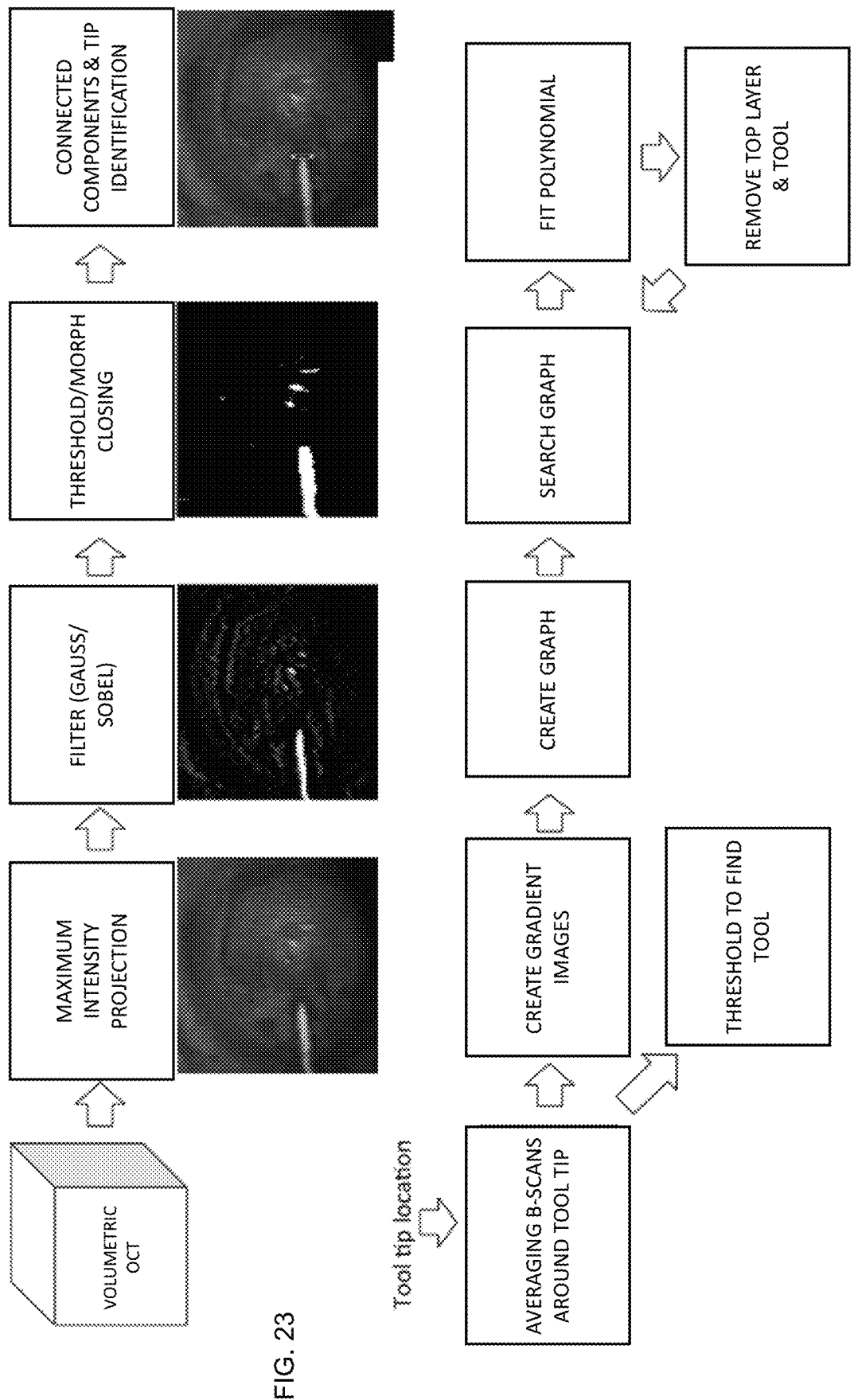
FIG. 23 is a flow chart showing an example method of tracking a tool in accordance with embodiments of the present disclosure.

For the bottom layer segmentation, the same steps as the top layer segmentation may be followed, but all vertices in the graph may be removed from the top layer segmentation and the tool. The tool may be removed from the search space prior to segmenting the bottom layer of the cornea because the bright tool creates large gradients, which the algorithm could mistake for the bottom layer. Even though surrounding B-scans are averaged, the signal to noise ratio of the cornea below the tool will still be low. For this reason, points in the segmentation may be removed that are to the left (right) of the tool tip before fitting a second order polynomial to the bottom layer. Once the tip is located and cornea layer boundaries segmented in the B-scan, the distance from the tool tip to the bottom layer of the cornea may be computed. An example method of tracking the tool is depicted in FIG. 23.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims. One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

REFERENCES

1. Aaker, G. D., L. Gracia, J. S. Myung, et al., *Volumetric three-dimensional reconstruction and segmentation of spectral-domain OCT*. Ophthalmic Surg Lasers Imaging, 2011. 42 Suppl (4): p. S116-20.
2. Schulze, J. P., C. Schulze-Dobold, A. Erginay, and R. Tadayoni, *Visualization of three-dimensional ultra-high resolution OCT in virtual reality*. Stud Health Technol Inform, 2013. 184: p. 387-91.
3. Kozak, I., P. Banerjee, J. Luo, and C. Luciano, *Virtual reality simulator for vitreoretinal surgery using integrated OCT data*. Clin Ophthalmol, 2014. 8: p. 669-72.
4. Shen, L., O. Carrasco-Zevallos, B. Keller, et al., *Novel Microscope-Integrated Stereoscopic Heads-up Display for Intrasurgical OCT in Ophthalmic Surgery*. Investigative Ophthalmology & Visual Science, 2015. 56(7): p. 3514-3514.
5. Ehlers, J. P., S. K. Srivastava, D. Feller, et al., *Integrative advances for OCT-guided ophthalmic surgery and intraoperative OCT: microscope integration, surgical instrumentation, and heads-up display surgeon feedback*. PLoS One, 2014. 9(8): p. e105224.

6. Viehland, C., B. Keller, O. M. Carrasco-Zevallos, et al., *Enhanced volumetric visualization for real time 4D intraoperative ophthalmic swept-source OCT*. Biomed Opt Express, 2016. 7(5): p. 1815-29.
7. Niemeyer, G. D., G. S. Guthart, W. C. Nowlin, N. Swamp, G. K. Toth, and R. G. Younge, *Camera referenced control in a minimally invasive surgical apparatus*, Dec. 30, 2003, U.S. Pat. No. 6,671,581.
8. Alvarez, J. B., J. Zhang, and A. Seam, *Method, apparatus and a system for robotic assisted surgery*, May 22, 2014, U.S. patent application Ser. No. 13/868,769.
9. Koreeda, Y., S. Obata, Y. Nishio, S. Miura, Y. Kobayashi, K. Kawamura, R. Souzaki, S. Ieiri, M. Hashizume, and M. G. Fujie. *Development and testing of an endoscopic pseudo-viewpoint alternating system, Int. J. Comput. Assit. Radiol. Surg.*, 10(5):619-628, May 2015.
10. Bichlmeier, C., S. M. Heining, M. Feuerstein, and N. Navab, *The virtual mirror: A new interaction paradigm for augmented reality environments, Medical Imaging, IEEE Transactions on*, 28(9):1498-1510, September 2009, ISSN 0278-0062, doi: 10.1109/TMI.2009.2018622.
11. LaRocca, F., Chiu, S. J., McNabb, R. P., Kuo, A. N., Izatt, J. A. and Farsiu, S., 2011. *Robust automatic segmentation of corneal layer boundaries in SDOCT images using graph theory and dynamic programming, Biomedical optics express*, 2(6), pp. 1524-1538.
12. Chiu, S. J., Li, X. T., Nicholas, P., Toth, C. A., Izatt, J. A. and Farsiu, S., 2010. *Automatic segmentation of seven retinal layers in SDOCT images congruent with expert manual segmentation, Optics express*, 18(18), pp. 19413-19428.
13. Kavraki, L. E., Svestka, P., Latombe, J. C. and Overmars, M. H., 1996. *Probabilistic roadmaps for path planning in high-dimensional configuration spaces*. IEEE transactions on Robotics and Automation, 12(4), pp. 566-580.
14. LaValle, S. M., 1998. *Rapidly-exploring random trees: A new tool for path planning*.
15. Shi, M., Liu, H. and Tao, G., 2002. *A stereo fluoroscopic image guided robotic biopsy scheme*. IEEE Transactions on Control Systems Technology, 10(3), pp. 309-317.

What is claimed:

1. A system comprising:
   a robotic tool interface configured to control a robotic tool;
   at least one controller configured to:
      receive an image dataset from an imaging system with an imaging perspective of an actual environment within which the robotic tool is positioned;
      generate a virtual environment of the actual environment based on the image dataset;
      control display of the virtual environment including a virtual tool controllable by a user for use to control the robotic tool within the actual environment;
      receive user input for controlling the virtual tool to control the robotic tool;
      output a command, based on the received input, to control movement of the robotic tool via the robotic tool interface;
      receive user input for altering a virtual perspective view of display of the virtual environment to another virtual perspective view that does not coincide with the imaging perspective;
      alter the display of the virtual environment from one of the one or more virtual perspective views to another virtual perspective view;
      provide simultaneous display of the actual environment from the imaging perspective and of the virtual environment from the other virtual perspective view; and
      maintain orientation of display of the virtual tool with respect to the user during display of the other virtual perspective view of the virtual environment.
2. The system of claim 1, wherein the image dataset is a three-dimensional (3D) image dataset.
3. The system of claim 1, wherein the environment is a surgical environment.
4. The system of claim 3, wherein the environment is an ocular surgical environment.
5. The system of claim 1, wherein the robotic tool comprises one of forceps, lighting equipment, syringe, scissors, irrigation equipment, suction equipment, scraper, probe, pick, and needle.
6. The system of claim 1, wherein the at least one controller is configured to:
   receive the image dataset in real time over a period of time; and
   generate and change the virtual environment in real time based on the real time receipt of the image dataset.
7. The system of claim 1, wherein the image dataset comprises one of an optical coherence tomography (OCT) image dataset, a magnetic resonance image (MRI) dataset, computed tomography (CT) image dataset, or an ultrasound image dataset.
8. The system of claim 1, wherein the at least one controller is configured to:
   specify one or more points for constraining movement of the robotic tool about the one or more points; and
   prevent movement of the robotic tool except about the one or more constraint points.
9. The system of claim 8, wherein the one or more points define a boundary for movement of the robotic tool.
10. The system of claim 8, wherein the one or more points define an axis pivot or plane of pivot for constraining translational motion of at least one portion of the robotic tool.
11. The system of claim 1, wherein the at least one controller is configured to specify one of a point, axis, or plane for constraining pivot movement of the robotic tool about the one of the point, axis, or plane.
12. The system of claim 1, wherein the at least one controller is configured to control a display to alternate between display of the first perspective view and the second perspective view.
13. The system of claim 1, wherein the second perspective view of the virtual environment substantially opposes the first perspective view of the virtual environment,
   wherein the at least one controller configured to:
      receive user input for moving the virtual tool in a direction; and
      move the virtual tool, in both the displayed first perspective and the second perspective, in the direction specified by the received user input for moving the virtual tool.
14. The system of claim 1, wherein the at least one controller comprises at least one processor and memory.
15. A method comprising:
   receiving an image dataset of an actual environment within which a robotic tool is positioned;
   generating a virtual environment of the actual environment based on the image dataset;

displaying the virtual environment including a virtual tool controllable by a user for use to control the robotic tool within the actual environment;

receiving user input for controlling the virtual tool to control the robotic tool;

controlling movement of the robotic tool based on the received input;

outputting a command, based on the received input, to control movement of the robotic tool via the robotic tool interface;

receiving user input for altering a perspective view of display of the virtual environment to another virtual perspective view that does not coincide with the imaging perspective;

altering the display of the virtual environment from one of the one or more virtual perspective views to another virtual perspective view;

providing simultaneous display of the actual environment from the imaging perspective and of the virtual environment from the other virtual perspective view; and maintaining orientation of display of the virtual tool with respect to the user during display of the other virtual perspective view of the virtual environment.

16. The method of claim 15, wherein the image dataset is a three-dimensional (3D) image dataset.

17. The method of claim 15, wherein the environment is a surgical environment.

18. The method of claim 15, wherein the environment is an ocular surgical environment.

19. The method of claim 15, wherein the robotic tool comprises one of forceps, lighting equipment, syringe, scissors, irrigation equipment, suction equipment, scraper, probe, pick, and needle.

20. The method of claim 15, wherein receiving the image dataset comprises receiving the image dataset in real time over a period of time; and wherein the method comprises generating and changing the virtual environment in real time based on the real time receipt of the image dataset.

21. The method of claim 15, wherein the image dataset comprises one of an optical coherence tomography (OCT) image dataset, a magnetic resonance image (MRI) dataset, computed tomography (CT) image dataset, or an ultrasound image dataset.

22. The method of claim 15, further comprising:

specifying one or more points for constraining movement of the robotic tool about the one or more points; and preventing movement of the robotic tool except about the one or more constraint points.

23. The method of claim 15, wherein the one or more points define a boundary for movement of the robotic tool.

24. The method of claim 15, wherein the one or more points define an axis pivot or plane of pivot for constraining translational motion of at least one portion of the robotic tool.

25. The method of claim 1, further comprising specifying one of a point, axis, or plane for constraining pivot movement of the robotic tool about the one of the point, axis, or plane.

26. The method of claim 15, further comprising controlling a display to alternate between display of the first perspective view and the second perspective view.

27. The method of claim 15, wherein the second perspective view of the virtual environment substantially opposes the first perspective view of the virtual environment, wherein the method further comprises:

receiving user input for moving the virtual tool in a direction; and moving the virtual tool, in both the displayed first perspective and the second perspective, in the direction specified by the received user input for moving the virtual tool.

* * * * *